United States Patent
Langhals et al.

(10) Patent No.: US 9,290,494 B2
(45) Date of Patent: Mar. 22, 2016

(54) SYSTEMS FOR THE LIGHT-INDUCED SEPARATION OF CHARGES

(75) Inventors: Heinz Langhals, Ottobrunn (DE); Andreas Obermeier, Bergkirchen (DE)

(73) Assignee: CYNORA GMBH, Eggenstein Leopoldshafen (DE)

( * ) Notice: Subject to any disclaimer, the term of this patent is extended or adjusted under 35 U.S.C. 154(b) by 1339 days.

(21) Appl. No.: 13/130,507

(22) PCT Filed: Nov. 23, 2009

(86) PCT No.: PCT/EP2009/008330
§ 371 (c)(1),
(2), (4) Date: Sep. 8, 2011

(87) PCT Pub. No.: WO2010/057669
PCT Pub. Date: May 27, 2010

(65) Prior Publication Data
US 2011/0318842 A1     Dec. 29, 2011

(30) Foreign Application Priority Data

Nov. 21, 2008 (DE) .......................... 10 2008 058 454
Oct. 9, 2009 (DE) .......................... 10 2009 048 906

(51) Int. Cl.
| | |
|---|---|
| C07D 471/08 | (2006.01) |
| H01L 51/46 | (2006.01) |
| C07D 471/06 | (2006.01) |
| C09K 11/06 | (2006.01) |
| H01L 51/00 | (2006.01) |
| H01L 51/42 | (2006.01) |
| H01L 51/50 | (2006.01) |

(52) U.S. Cl.
CPC .............. *C07D 471/06* (2013.01); *C09K 11/06* (2013.01); *H01L 51/0053* (2013.01); *C09K 2211/1007* (2013.01); *C09K 2211/1033* (2013.01); *C09K 2211/1044* (2013.01); *H01L 51/42* (2013.01); *H01L 51/5012* (2013.01); *Y02E 10/549* (2013.01); *Y10T 436/201666* (2015.01)

(58) Field of Classification Search
USPC ............................................. 546/37; 313/504
See application file for complete search history.

(56) References Cited

FOREIGN PATENT DOCUMENTS

WO    PCTEP2009008330      4/2010

OTHER PUBLICATIONS

Langhals, H. et al.: Light-driven charge separation in isoxazolidine-perylene bisimide dyads. Chem. Eur. J. , vol. 15, pp. 12733-12744, 2009.*

E.E. Neuteboom et al., "Alternating Oligo(p-phenylene vinylene)-Perylene Bisimide Copolymers: Synthesis, Photophysics, and Photovoltaic Properties of a New Class of Donor-Acceptor Materials," Journal of the American Chemical Society, Jun. 2003, pp. 8625-8638, vol. 125, No. 28.

X. Li et al., "Ultrafast Aggregate-to-Aggregate Energy Transfer Within Self-Assembled Light-Harvesting Columns of Zinc Phthalocyanine Tetrakis(Perylenediimide)," Journal of the American Chemical Society, Aug. 2004, pp. 10810-10811, vol. 126, No. 35.

L. Flamigni et al., "New and Efficient Arrays for Photoinduced Charge Separation Based on Perylene Bisimide and Corroles," Chemistry—A European Journal, Oct. 2007, pp. 169-183, vol. 14., No. 1.

H. Langhals et al., "A Click Reaction for Fluorescent Labelling: Application of the 1,3-Dipolar Cycloaddition Reaction," European Journal of Organic Chemistry, Nov. 2008, pp. 6144-6151, vol. 2008, No. 36.

H. Langhals et al., "The Identification of Carbonyl Compounds by Fluorescence: A Novel Carbonyl-Derivatizing Reagent," Chemistry—A European Journal, Nov. 1998, pp. 2110-2116, vol. 4, No. 11.

H. Langhals et al., "An Approach to Novel NIR Dyes Utilising α-Effect Donor Groups," Dyes and Pigments, Nov. 2003, pp. 109-116, vol. 59, No. 2.

* cited by examiner

*Primary Examiner* — Charanjit Aulakh
(74) *Attorney, Agent, or Firm* — Ryan, Mason & Lewis, LLP

(57) ABSTRACT

Organic systems having a light-absorbing unit and a unit causing separation of charges are described. Said organic systems efficiently separate charges induced by light and have high lightfastness.

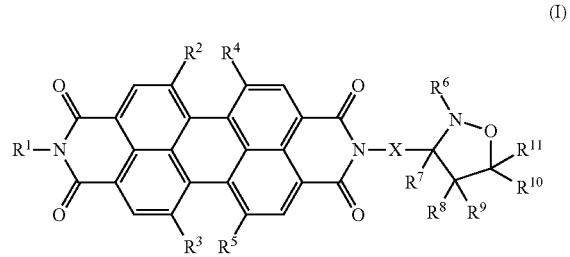

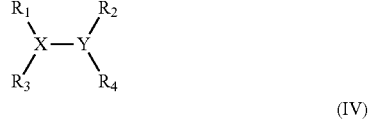

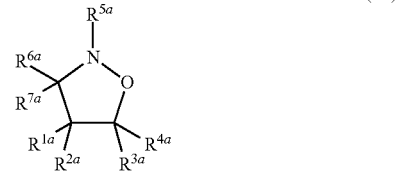

10 Claims, 5 Drawing Sheets

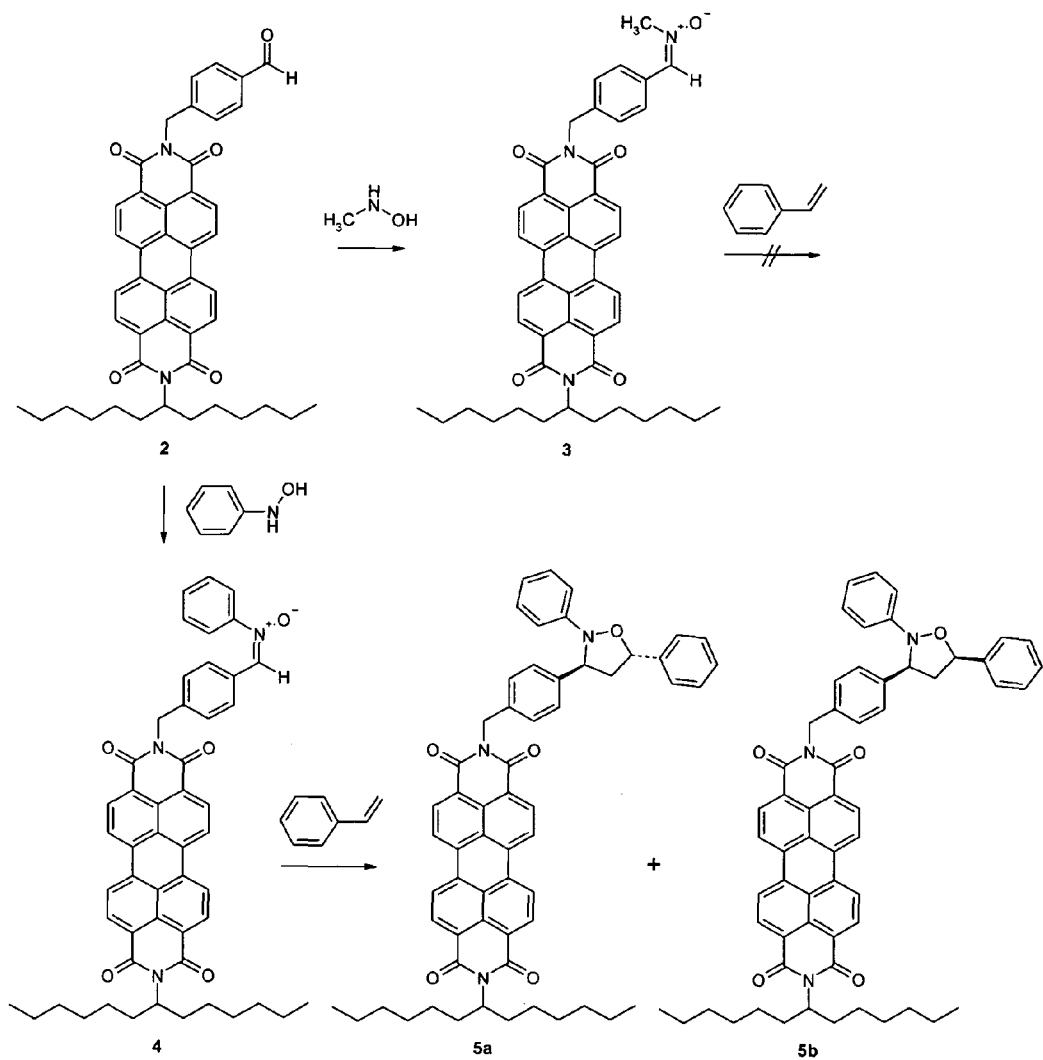
Figur 1.

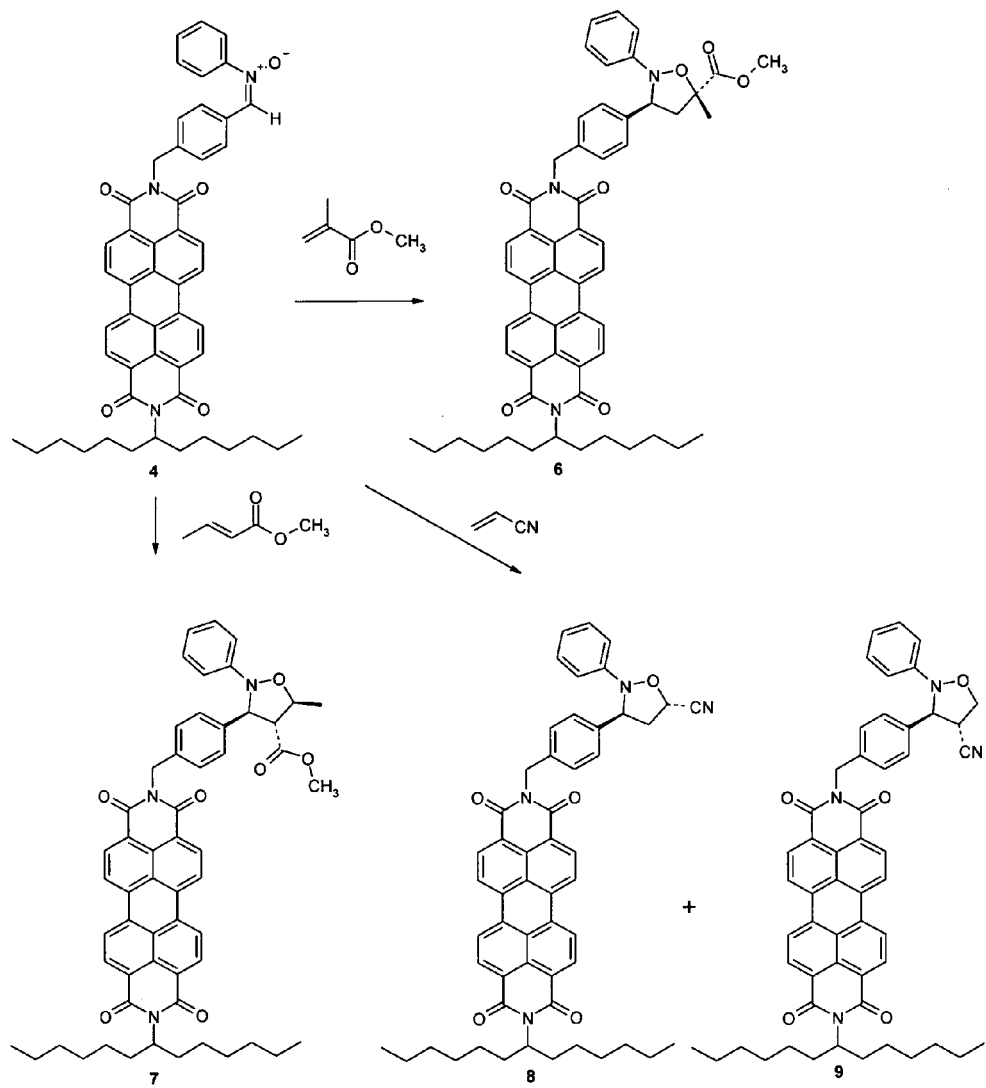
Figur 2.

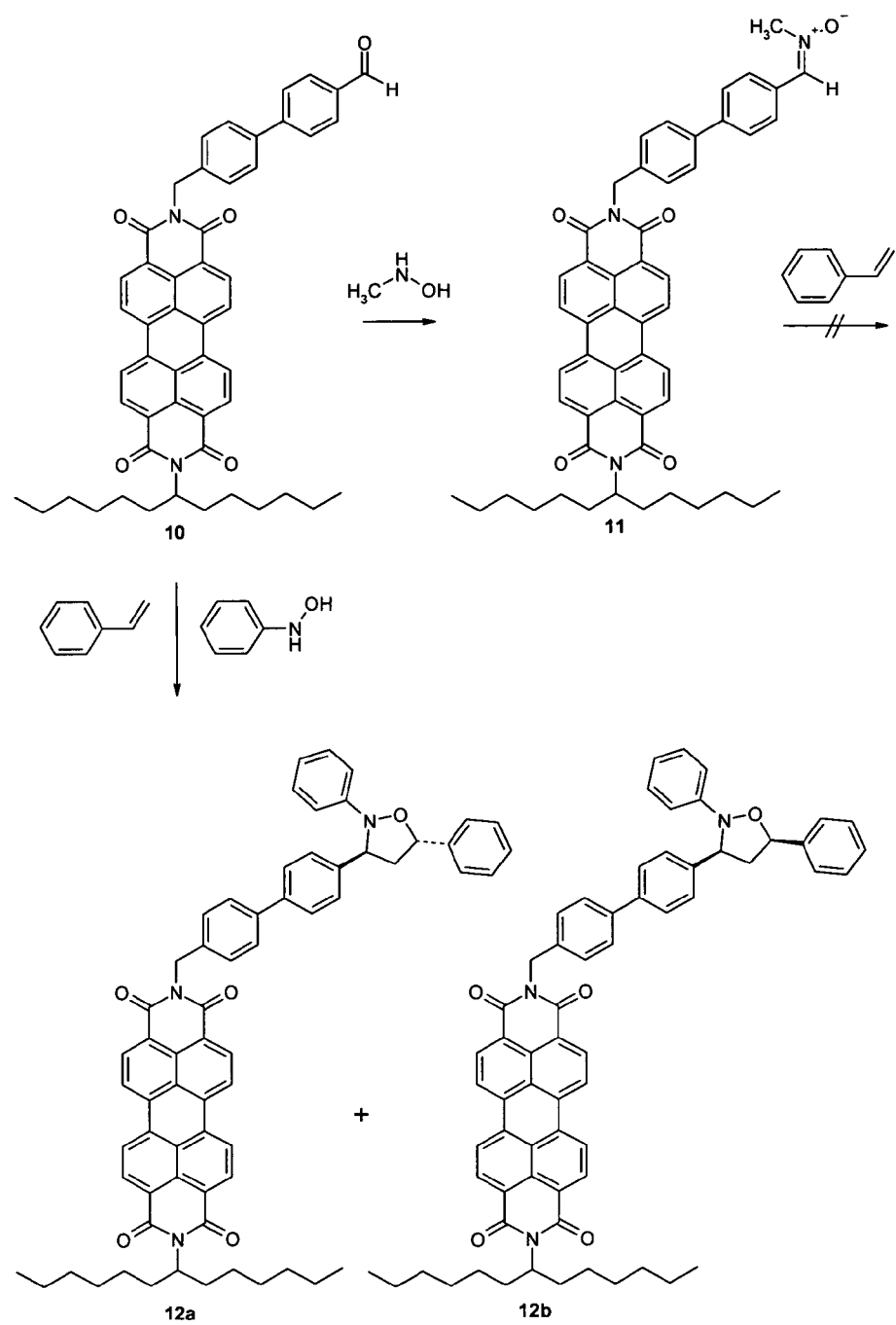
Figur 3.

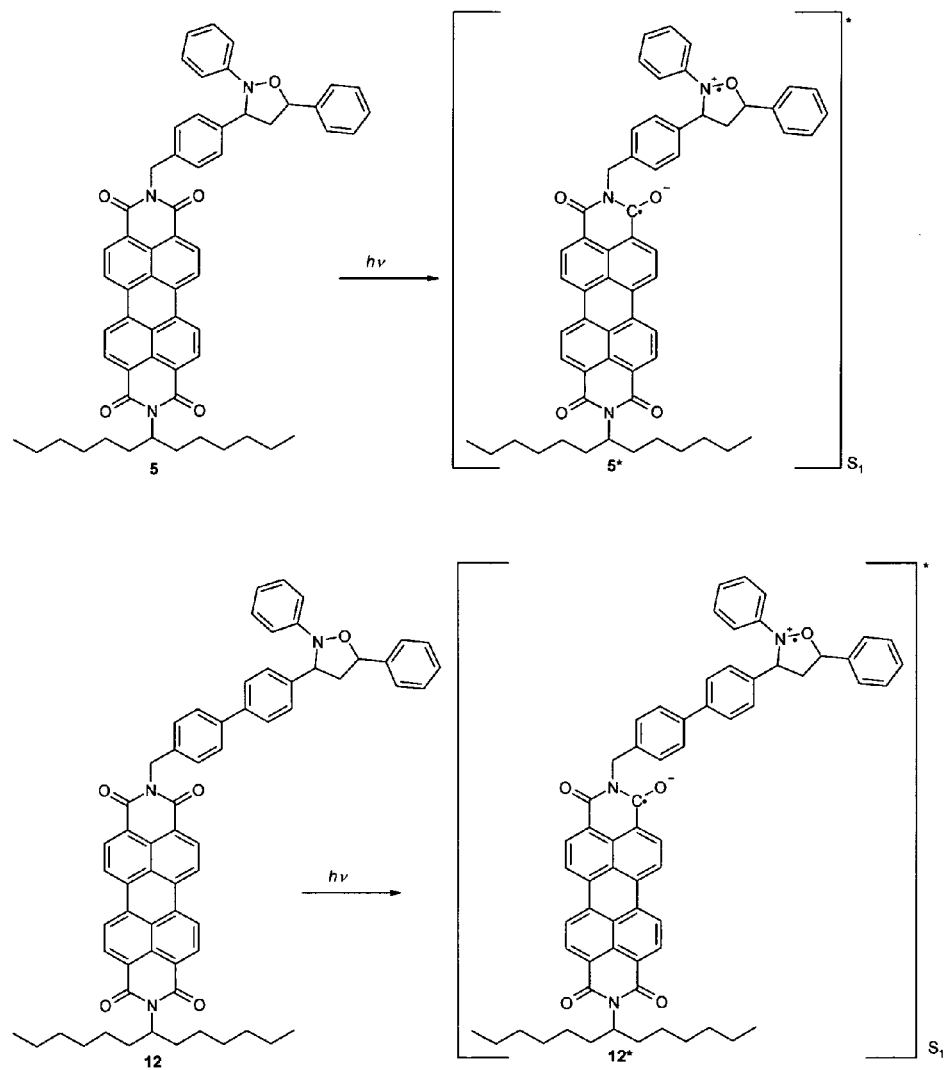
Figur 4.

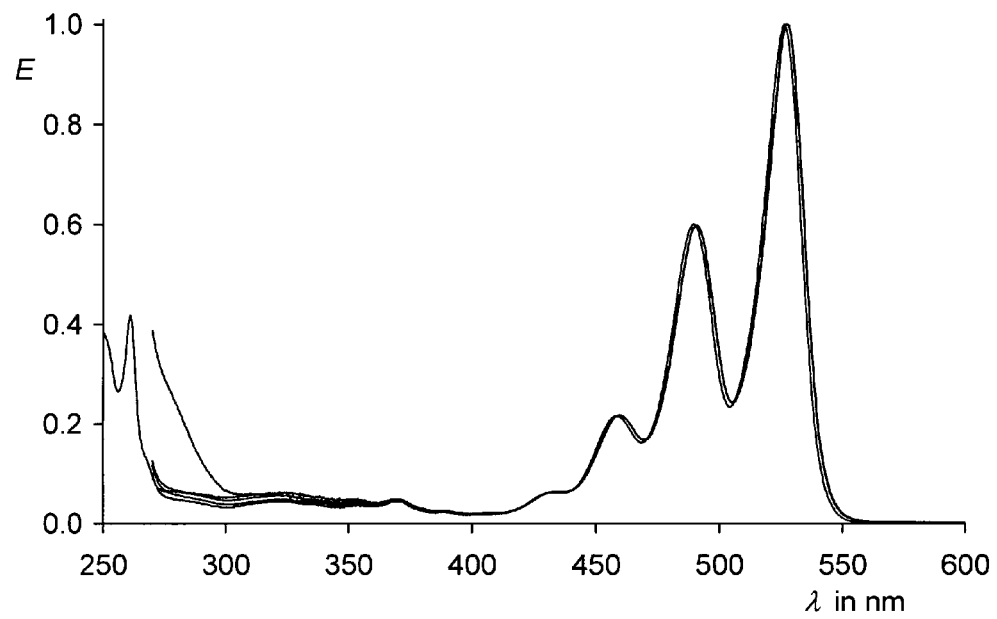
Figur 5

SYSTEMS FOR THE LIGHT-INDUCED SEPARATION OF CHARGES

Light-driven separation of electric charges is attracting increasing interest in basic scientific research and in technology. The prospect here is that of efficiently collecting solar energy and converting it into electrical energy. Organic materials are exceptionally interesting for future development as light-absorbing structures, since with them it is possible to realize intensely colored chromophores that may be easily modified within wide limits and adapted to specific requirements. In addition, organic materials may be recycled or disposed of without problems, a consideration that is becoming more and more significant for longer-term developments. Only a limited number of such compounds has hitherto been available, however. The long-term stability of such systems is an unsolved problem. A universal, light-fast system for light-induced generation of charge separation would represent substantial progress.

What is required for light-driven charge separation is a light-absorbing unit (hereinafter also called a "chromophore") and a structure that brings about the charge separation. In principle, both units may be constructed from chromophores, as has been realized in previous work (L. Flamigni, B. Ventura, M. Tasior, T. Becherer, H. Langhals, D. T. Gryko, Chem. Eur. J. 2008, 14, 169-183; M. Tasior, D. T. Gryko, Jing Shen, K. M. Kadish, T. Becherer, H. Langhals, B. Ventura, L. Flamigni, J. Phys. Chem. C 2008, published online Nov. 17, 2008; JP8065635). The fundamental problem existing here, however, is that the two chromophores must be optimized both for light absorption and for charge separation. Such a strategy leads to many compromises that must be addressed. A further fundamental problem which exists is that the extinction coefficients of the individual chromophores must be coordinated with one another because the chromophores are linked to each other, so that the light absorption capability of the ultimate arrangement cannot be controlled by way of the relative concentration of the components.

Structures that are made up of a chromophore and a colorless molecule part, constituting a substituent on the chromophore, that is intended to bring about charge separation, still require further development. An electron transfer after optical excitation requires a high orbital, whether a π or n orbital, for example the n orbital of free amines. The optical excitation creates an electron hole in the HOMO of the dye which is then filled by electron transfer proceeding from the high orbital of the substituent, so that it becomes impossible for the excited electron to return, for example with fluorescent light emission. As a result, fluorescence quenching is both a consequence and a very good indicator of the electron transfer reaction. An amino group bound directly onto the carboxylic acid imide nitrogen atom results in fluorescence quenching (H. Langhals, W. Jona, Chem. Eur. J. 1998, 4, 2110-2116) and verifies this process. The amino group and the chromophore are, however, very closely adjacent, so that return transfer occurs quickly and it is thus almost impossible to utilize the charge separation. If a spacer is introduced between the amino group and the chromophore, the disappointing result is that this electron process comes to a complete standstill, and the substances fluoresce almost 100% (H. Langhals, A. Obermeier, Eur. J. Org. Chem. 2008, 6144-6151). The question that arises here is whether the electron donor properties of the group may be enhanced sufficiently that electron transfer may be switched back on even with a greater spacing.

Against this background, the object of the present invention was to develop organic structures in which it is possible to achieve light-driven charge separation in efficient fashion. The light fastness of such structures was, in this context, of central importance.

According to the present invention, this object is achieved with compounds of the following general formula I, which are also referred to as perylene bisimide dyads.

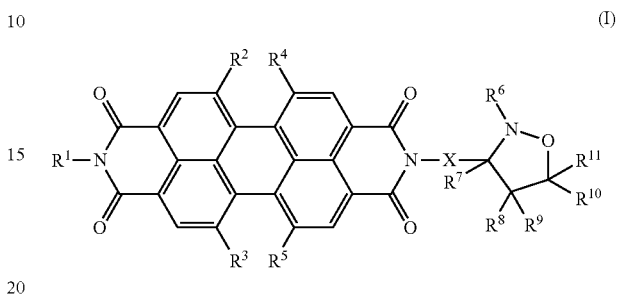

The meaning of substituents $R^1$ to $R^{11}$, and of grouping X, is explained in further detail below.

In addition, the present invention makes available perylenetetracarboxylic acid bisimide nitrones of the general formula (II),

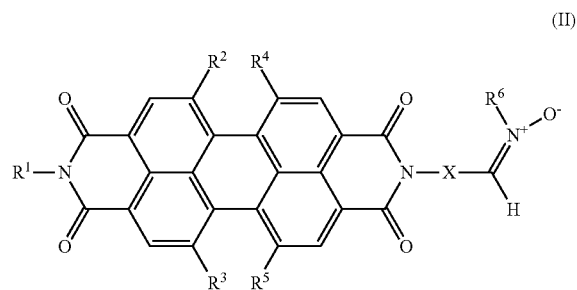

in which substituents $R^1$ to $R^6$ and X, each independently, have the same meaning as for compounds of formula (I).

According to a further aspect, the invention relates to the use of α-effect compounds of the general formula (III) as electron donor groups in light-driven systems for charge separation,

X and Y, as well as substituents $R_1$ to $R_4$, likewise being explained below.

Lastly, according to a further aspect, the invention relates to the use of isoxazolidines of the general formula (IV) as electron donor groups in light-driven systems for charge separation,

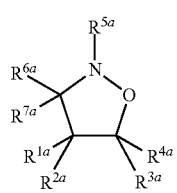

(IV)

substituents $R^{1a}$ to $R^{7a}$ likewise being explained below.

BRIEF DESCRIPTION OF DRAWINGS

FIG. 1 shows, by way of example, the synthesis of nitrones 3 and 4 and the reaction of 4 with styrene to yield oxazolidines 5a and 5b.

FIG. 2 shows, by way of example, the synthesis of oxazolidines 6 to 9.

FIG. 3 shows, by way of example, the synthesis of nitrone 11 and of oxazolidines 12a and 12b.

FIG. 4 shows ground states and electronically excited states of 5 and 12.

FIG. 5 shows UV/Vis absorption and fluorescence spectra of the isoxazolidines (identical above 400 nm) compared with 1a (R=1-hexylheptyl) which appears to be approximately half a nanometer shorter in wavelength. From top to bottom at 300 nm: 12, 1a, 5, 6, and 7.

It was found in the context of the invention that it is advantageous to link a single chromophore to a colorless structure in order to achieve charge separation.

As discussed below, the perylene-3,4:9,10-tetracarboxylic acid bisimides that are depicted schematically in formula 1 below,

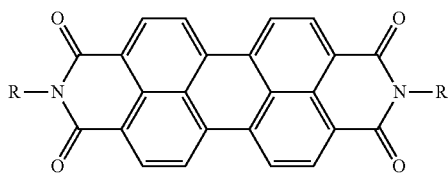

1 as well as derivatives thereof, were identified as particularly suitable chromophores. They are notable for high absorption coefficients, and their great light fastness and chemical resistance (H. Langhals, Helv. Chim. Acta 2005, 88, 1309-1343; H. Langhals, Heterocycles 1995, 40, 477-500; H. Langhals, Molecular Devices. Chiral, Bichromophoric Silicones: Ordering Principles in Complex Molecules in F. Ganachaud, S. Boileau, B. Boury (eds.), Silicon Based Polymers, p. 51-63, Springer, 2008, ISBN 978-1-4020-8527-7, e-ISBN 978-1-4020-8528-4).

Their high fluorescence quantum yields (H. Langhals, J. Karolin, L. B. -A. Johansson, J. Chem. Soc, Faraday Trans. 1998, 94, 2919-2922) of almost 100% are advantageous for the development of systems with light-driven charge separation, since the optical excitation energy is thereby obtained for processes occurring subsequently. The nitrogen atoms of 1 are ideal linkage points for constructing the rest of the structure. In order to promote the solubility of the perylene bisimides, a solubility-increasing 1-hexylheptyl substituent ("swallowtail" substituent; compound 1a has the formula I presented above, both substituents denoting a 1-hexylheptyl substituent) may be used, for example, for one of the substituents R (S. Demmig, H. Langhals, Chem. Ber. 1988, 121, 225-230; H. Langhals, S. Demmig, T. Potrawa, J. Prakt. Chem. 1991, 333, 733-748). Linkage to the additional functional structures may be performed, for example, using the second substituent R. In addition, further substituents on the perylene skeleton may be introduced.

In the colorless groups that are used to bring about a charge separation, which in systems according to the present invention for light-driven charge separation are connected to a chromophore, it was possible in the context of the invention to use the α-effect to prevent fluorescence quenching of the charge separation. A group having two atoms bound directly to one another, both of which carry free electron pairs, are used to this end in order to bring about the charge separation. A combination of nitrogen with oxygen is of particular interest here. By using isoxazolidines (P. Grünanger, P. Vita-Finzi, Isoxazolidines, in The Chemistry of Heterocyclic Compounds (E. C. Tayloer, A. Weissberger, editors) Vol. 49/1, pp. 649-877, Wiley, New York 1991, ISBN 0-471-02233-0; S. Cicchi, F. M. Cordero, D. Giomi, Five-membered ring Systems: with O & N atoms in Progress in Heterocyclic Chemistry 2003, 15, 261-283; Y. Takeuchi, F. Furusaki, The chemistry of isoxazolidines in Advances in Heterocyclic Chemistry 1977, 21, 207-251), additional stability may be imparted to a structure of this kind by incorporation into a ring.

As stated above, according to a first aspect the present invention makes available perylene bisimide dyads of the general formula (I).

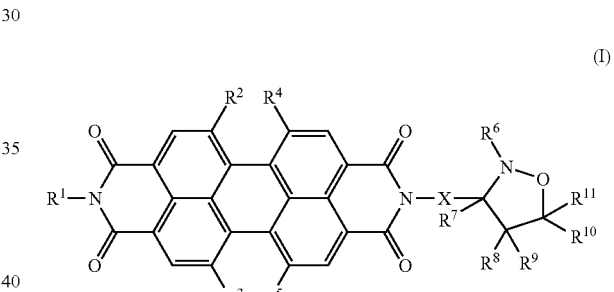

(I)

In this formula, substituents $R^1$ to $R^{11}$ are identical or different and denote, each independently, hydrogen or a linear alkyl substituent having at least one and at most 37 carbon atoms. In the alkyl substituent, one to 10 $CH_2$ units may be replaced, each independently, by a carbonyl group, an oxygen atom, sulfur atom, selenium atom, tellurium atom, a cis or trans CH=CH group in which one CH unit may also be replaced by a nitrogen atom, an acetylenic C≡C group, a divalent phenyl substituent (e.g. 1,2-, 1,3- or 1,4-phenyl substituent), divalent pyridine substituent (e.g. 2,3-, 2,4-, 2,5-, 2,6-, 3,4- or 3,5-pyridine substituent), divalent thiophene substituent (e.g. 2,3-, 2,4-, 2,5- or 3,4-thiophene substituent), divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. Up to 12 individual hydrogen atoms of the $CH_2$ groups may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), a divalent thiophene substituent (e.g. 2,3-, 2,4-, 2,5- or 3,4-thiophene substituent), a divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. Up to 12 individual hydrogen atoms of the $CH_2$ groups in an alkyl substituent may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), a divalent thiophene substituent (e.g. 2,3-, 2,4-, 2,5- or 3,4-thiophene substituent), a divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. $CH_2$ groups on which a hydrogen atom is replaced as described above may also be linked to one another to form a ring, i.e. instead of carrying substituents, the free valences of the methine groups or of the quaternary carbon atoms may be linked in pairs so that rings such as, for example, cyclohexane rings are produced. Substituents $R^1$ to $R^5$ and $R^7$ to $R^{11}$ may moreover represent, each independently, the halogen atoms F, Cl, Br or I, or CN.

X in formula (I) signifies one to 12 $CH_2$ units in which, each independently, one or more may be replaced respectively by a carbonyl group, an oxygen atom, sulfur atom, selenium atom, tellurium atom, a cis or trans CH=CH group in which one CH unit may also be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), divalent thiophene substituent (e.g. 2,3-, 2,4-, 2,5- or 3,4-thiophene substituent), divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which'one or two CH groups may be replaced by nitrogen atoms. Up to 12 individual hydrogen atoms of the $CH_2$ groups may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), a divalent thiophene substituent (e.g. 2,3-, 2,4-, 2,5- or 3,4-thiophene substituent), a divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. Up to 12 individual hydrogen atoms of the $CH_2$ groups of the alkyl substituents may be replaced, in each case each independently even on identical carbon atoms, by the halogens fluorine, chlorine, bromine, or iodine, a cyano group, or, a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), divalent pyridine substituent (e.g. 2,3-, 2,4-, 2,5-, 2,6-, 3,4- or 3,5-pyridine substituent), divalent thiophene substituent (e.g. 2,3-, 2,4-, 2,5- or 3,4-thiophene substituent), divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. $CH_2$ groups on which a hydrogen atom is replaced as described above may also be linked to one another to form a ring, i.e. instead of carrying substituents, the free valences of the methine groups or of the quaternary carbon atoms may be linked in pairs so that rings such as, for example, cyclohexane rings are produced.

Unless otherwise indicated, in the context of this description a $CH_2$ unit that by definition may be replaced may also be a terminal unit in an alkyl substituent or alkyl chain, i.e. a corresponding unit within a —$CH_3$ group. For example, the reference to a divalent ring or divalent ring system that may replace a $CH_2$ unit (e.g. divalent phenyl substituents or 1,2-, 1,3- or 1,4-phenyl substituents) is also to be understood here and hereinafter to mean that one of the two valences may also be saturated with a hydrogen atom. This also encompasses the situation in which, starting with a methyl group by replacement of a formal $CH_2$ unit contained therein, a phenyl substituent, pyridine substituent, thiophene substituent, etc. is present at the corresponding position. Substituents $R^1$ to $R^{11}$ may therefore also, in the context of the preceding definition, also represent e.g. aryl substituents, in particular phenyl or naphthyl substituents, heteroaryl substituents, in particular pyridyl or thiophenyl substituents, aralkyl substituents, and heteroaralkyl substituents.

In formula (I), substituent $R^1$ is preferably hydrogen or one of the hydrocarbon substituents recited in the general definition. An alkyl, alkenyl, or alkynyl substituent is particularly preferred. Both linear substituents and branched substituents are included in this context; in the case of the branched substituents as described above, one or more hydrogen atoms of $CH_2$ groups are replaced by further alkyl chains that may likewise contain a double or triple bond. The total number of carbon atoms in these alkyl, alkenyl or alkynyl substituents is preferably 6 to 20. Particularly preferred as $R^1$ is a linear or branched alkyl substituent according to the above definition that comprises 6 to 20 carbon atoms.

Substituents $R^2$ to $R^5$ are preferably selected, each independently, from hydrogen or one of the hydrocarbon substituents recited in the general definition. An alkyl, alkenyl, or alkynyl substituent is particularly preferred. Both linear substituents and branched substituents are included in this context; in the case of the branched substituents, as described above, one or more hydrogen atoms of $CH_2$ groups are replaced by further alkyl chains that may likewise contain a double or triple bond. Particularly preferred in addition is an aryl substituent, e.g. phenyl. The total number of carbon atoms in these substituents is preferably 1 to 20 for alkyl, alkenyl, and alkynyl substituents, and 6 to 14 for the aryl substituent. $R^2$ to $R^5$ are particularly preferably hydrogen or a linear or branched alkyl substituent according to the definition above that comprises one to 10 carbon atoms, in particular hydrogen.

$R^6$ is preferably selected from hydrogen, an alkyl substituent, an aryl substituent, heteroaryl substituent, aralkyl substituent, or heteroarylalkyl substituent. $R^6$ is particularly preferably an aryl substituent or heteroaryl substituent, in particular an aryl substituent.

The alkyl substituent, or the alkyl portion of these preferred substituents, comprises a linear chain of 1 to 20 carbon atoms. It may be substituted with one or more substituents, e.g. one, two, or three, selected from linear alkyl chains having up to 10 carbon atoms, Cl, Br, or CN, but is preferably unsubstituted.

The aryl substituent, or the aryl portion of the aralkyl substituent, is preferably phenyl or naphthyl, in particular phenyl. The heteroaryl substituent, or the heteroaryl portion of the heteroaralkyl substituent, is preferably pyridine or thiophene.

$R^7$ is preferably selected from hydrogen or an aryl substituent having up to 10 carbon atoms, Cl, Br, or CN. Particularly preferably, $R^7$ is hydrogen.

Substituents $R^8$ to $R^{11}$ are preferably selected, each independently, from hydrogen, an alkyl substituent, an alkoxy substituent, an aryl substituent, heteroaryl substituent, aralkyl substituent, or heteroaralkyl substituent, Cl, Br, or CN.

The alkyl substituent, or the alkyl portion of these substituents, preferably comprises a linear chain of 1 to 20 carbon atoms. It may be substituted with one or more substituents, e.g. one, two, or three, selected from linear alkyl chains having up to 10 carbon atoms, Cl, Br, or CN, but is preferably unsubstituted.

The aryl substituent, or the aryl portion of the aralkyl substituent, is preferably phenyl or naphthyl. The heteroaryl substituent, or the heteroaryl portion of the heteroaralkyl substituent, is preferably pyridine or thiophene.

Preferably at least one of substituents $R^8$ and $R^9$ and at least one of substituents $R^{10}$ and $R^{11}$ is hydrogen; particularly preferably, three of substituents $R^8$ to $R^{11}$ are hydrogen. In addition, one of substituents $R^{10}$ and $R^{11}$ is preferably an aryl substituent or heteroaryl substituent, particularly preferably an aryl substituent.

X is preferably selected from one to 12 methylene units, such that one or more $CH_2$ groups may be replaced by a group selected independently from O, S, and phenylene. Particularly preferably, X is formed from one or two phenylene groups or a bisphenylene group in combination with one to four, preferably one or two, methylene units.

For the perylenetetracarboxylic acid bisimide nitrones of the general formula (II),

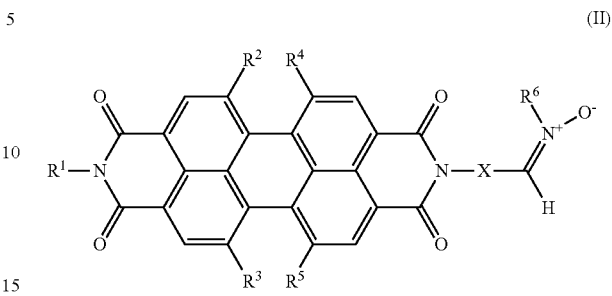

the definitions of substituents $R^1$ to $R^6$ and X, including the definitions of preferred substituents, correspond to those that were given for substituents $R^1$ to $R^6$ and X with reference to formula (I).

According to a further aspect, the present invention makes available the use of α-effect compounds of the general formula (III) as electron donor groups in light-driven systems for charge separation.

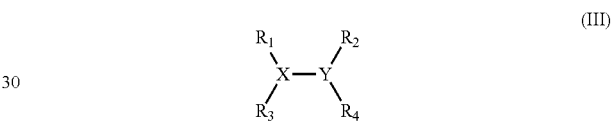

In formula (III), X and Y are identical or different and represent elements having free, non-binding electron pairs, preferably elements of the second and third period such as nitrogen, oxygen, fluorine, sulfur, and chlorine, preferably the elements of the second period, and of these most preferably nitrogen and oxygen. Substituents $R_1$ to $R_4$ are identical to or different from one another and represent, each independently, hydrogen or linear alkyl substituents having at least one and at most 37 carbon atoms. It is evident to one skilled in the art that depending on which element is selected for X and Y, one of substituents $R_1$ and $R_3$, or one of substituents $R_2$ and $R_4$, may be absent. In the alkyl substituent, one to 10 $CH_2$ units may be replaced, each independently, by a carbonyl group, an oxygen atom, sulfur atom, selenium atom, tellurium atom, a cis or trans CH=CH group in which one CH unit may also be replaced by a nitrogen atom, an acetylenic C≡C group, a divalent phenyl substituent (e.g. 1,2-, 1,3- or 1,4-phenyl substituent), divalent pyridine substituent (e.g. 2,3-, 2,4-, 2,5-, 2,6-, 3,4- or 3,5-pyridine substituent), divalent thiophene substituent (e.g. 2,3-, 2,4-, 2,5- or 3,4-thiophene substituent), divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. Up to 12 individual hydrogen atoms of the $CH_2$ groups may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), a divalent thiophene substituent (e.g. 2,3-, 2,4-, 2,5- or 3,4-thiophene substituent), a divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. Up to 12 individual hydrogen atoms of the $CH_2$ groups in an alkyl substituent may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), a divalent thiophene substituent (e.g. 2,3-, 2,4-, 2,5- or 3,4-thiophene substituent), a divalent naphthalene substituent (e.g. 1,2-, 1,3-, 1,4-, 1,5-, 1,6-, 1,7-, 1,8-, 2,3-, 2,6- or 2,7- naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. $CH_2$ groups on which a hydrogen atom is replaced as described above may also be linked to one another to form a ring, i.e. instead of carrying substituents, the free valences of the methine groups or of the quaternary carbon atoms may be linked in pairs so that rings such as, for example, cyclohexane rings are produced. Substituents $R_1$ to $R_4$ may moreover, each independently, represent the halogen atoms F, Cl, Br, or I, or CN. Substituents $R_1$ and $R_2$ or substituents $R_3$ and $R_4$ are preferably connected with ring closure, thus forming, together with X and Y, a five- or six-membered ring.

As already indicated for formula (I), in the context of this description a $CH_2$ unit that by definition may be replaced may also be a terminal unit in an alkyl substituent or alkyl chain, i.e. a corresponding unit within a —$CH_3$ group. Substituents $R_1$ to $R_4$ may therefore, in the context of the preceding definition, also represent e.g. aryl substituents, in particular phenyl or naphthyl substituents, heteroaryl substituents, in particular pyridyl or thiophenyl substituents, aralkyl substituents, and heteroaralkyl substituents.

The above-described use of the α-effect compounds of the general formula (III) as electron donor groups in light-driven systems for charge separation is usually effected in such a way that the compound is bound via any one of substituents $R_1$ to $R_4$ to a light-absorbing unit, typically via a covalent bond. Known structures that absorb in a spectral region suitable for the respective application may be used as a light-absorbing unit, also referred to as a chromophore. The invention to that extent also contains compounds, constituting systems for charge separation, made up of a light-absorbing unit and an electron donor group that may be derived formally from a compound of formula (III) by abstracting an atom, typically a hydrogen atom, from any one of substituents $R_1$ to $R_4$ so that the relevant substituent forms a linker group that connects the compound of formula (III) to the chromophore.

According to a further, preferred aspect, the present invention makes available the use of α-effect compounds of the general formula (IIIa) as electron donor groups in light-driven systems for charge separation.

(IIIa)

In formula (IIIa), X and Y are identical or different and represent elements having a free, non-binding electron pair, selected from nitrogen, oxygen, and sulfur, preferably from nitrogen and oxygen. If X is oxygen or sulfur, $R_{1a}$ is then absent. If Y is oxygen or sulfur, $R_{2a}$ is then absent. If they are present, substituents $R_{1a}$ and $R_{2a}$ denote hydrogen, an alkyl substituent, in particular methyl, ethyl, propyl, or butyl, or a phenyl substituent. Substituents $R_{3a}$ and $R_{4a}$ form, together with X and Y, a five- or six-membered ring that encompasses as ring atoms, in addition to the elements X and Y, carbon and optionally one or more further heteroatoms selected from S, N, and O. The ring formed from $R_{3a}$ and $R_{4a}$ may be saturated or may encompass a carbon-carbon or carbon-nitrogen double bond.

The above-described use of the α-effect compounds of the general formula (IIIa) as electron donor groups in light-driven systems for charge separation is usually effected in such a way that the compound is bound via any one of substituents $R_{1a}$ to $R_{4a}$ to a light-absorbing unit, typically via a covalent bond. Known structures that absorb in a spectral region suitable for the respective application may be used as a light-absorbing unit, also referred to as a chromophore. The invention in that respect also contains compounds, constituting systems for charge separation, made up of a light-absorbing unit and an electron donor group that may be derived formally from a compound of formula (IIIa) by abstracting an atom, typically a hydrogen atom, from any one of substituents $R_{1a}$ to $R_{4a}$ so that the relevant substituent forms a linker group that connects the compound of formula (IIIa) to the chromophore.

The invention also encompasses, in particular, the use of isoxazolidines of the general formula (IV) as electron donor groups in light-driven systems for charge separation.

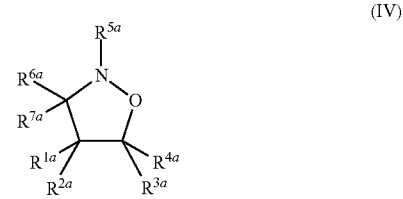

(IV)

In formula (IV), substituents $R^{1a}$ to $R^{7a}$ are identical to or different from one another and represent, each independently, hydrogen or linear alkyl substituents having at least one and at most 37 carbon atoms. In the alkyl substituent, one to 10 $CH_2$ units may be replaced, each independently, by a carbonyl group, an oxygen atom, sulfur atom, selenium atom, tellurium atom, a cis or trans CH=CH group in which one CH unit may also be replaced by a nitrogen atom, an acetylenic C≡C group, a divalent phenyl substituent (e.g. 1,2-, 1,3- or 1,4- phenyl substituent), divalent pyridine substituent (e.g. 2,3-, 2,4-, 2,5-, 2,6-, 3,4- or 3,5-pyridine substituent), divalent thiophene substituent (e.g. 2,3-, 2,4-, 2,5- or 3,4-thiophene substituent), divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. Up to 12 individual hydrogen atoms of the $CH_2$ groups may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), a divalent thiophene substituent (e.g. 2,3-, 2,4-, 2,5- or 3,4-thiophene substituent), a divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. Up to 12 individual hydrogen atoms of the $CH_2$ groups in an alkyl substituent may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent (e.g. 1,2-, 1,3- or 1,4-phenyl substituent), a divalent pyridine substituent (e.g. 2,3-, 2,4-, 2,5-, 2,6-, 3,4- or 3,5-pyridine substituent), a divalent thiophene substituent (e.g. 2,3-, 2,4-, 2,5- or 3,4-thiophene substituent), a divalent naphthalene substituent (e.g. 1,2-, 1,3-, 1,4-, 1,5-, 1,6-, 1,7-, 1,8-, 2,3-, 2,6- or 2,7-naphthalene substituent) in which one or two CH groups may be replaced by nitrogen atoms, and a divalent anthracene substituent (e.g. 1,2-, 1,3-, 1,4-, 1,5-, 1,6-, 1,7-, 1,8-, 1,9-, 1,10-, 2,3-, 2,6-, 2,7-, 2,9-, 2,10- or 9,10-anthracene substituent) in which one or two CH groups may be replaced by nitrogen atoms. $CH_2$ groups on which a hydrogen atom is replaced as described above may also be linked to one another to form a ring, i.e. instead of carrying substituents, the free valences of the methine groups or of the quaternary carbon atoms may be linked in pairs so that rings such as, for example, cyclohexane rings are produced. Substituents $R^{1a}$ to $R^{4a}$, $R^{6a}$, and $R^{7a}$ may moreover represent, each independently, the halogen atoms F, Cl, Br, or I, or CN.

As already indicated for formula (I), in the context of this description a $CH_2$ unit that by definition may be replaced may also be a terminal unit in an alkyl substituent or alkyl chain, i.e. a corresponding unit within a —$CH_3$ group. Substituents $R^{1a}$ to $R^{7a}$ may therefore, in the context of the preceding definition, also represent e.g. aryl substituents, in particular phenyl or naphthyl substituents, heteroaryl substituents, in particular pyridyl or thiophenyl substituents, aralkyl substituents, and heteroaralkyl substituents.

As a rule, the above-described use of the isoxazolidines of the general formula (IV) as electron donor groups in light-driven systems for charge separation is effected in such a way that the compound is bound via one of substituents $R^{1a}$ to $R^{7a}$ to a light-absorbing unit, typically via a covalent bond. This bonding is effected preferably via one of substituents $R^{1a}$ to $R^{4a}$, $R^{6a}$, or $R^{7a}$, particularly preferably via substituent $R^{6a}$. Known structures that absorb in a spectral region suitable for the particular application may be used as a light-absorbing unit, also referred to as a chromophore. The invention thus also contains compounds, constituting systems for charge separation, made up of a light-absorbing unit and an electron donor group that may be derived formally from a compound of formula (IV) by abstracting an atom, typically a hydrogen atom, from any one of substituents $R^{1a}$ to $R^{7a}$, preferably from one of substituents $R^{1a}$ to $R^{4a}$, $R^{6a}$, or $R^{7a}$, particularly preferably from substituent $R^{6a}$, so that the relevant substituent forms a linker group that connects the compound of formula (IV) to the chromophore.

Substituents $R^{1a}$ to $R^{4a}$ are preferably selected, each independently, from hydrogen, an alkyl substituent, an-alkoxy substituent, an aryl substituent, heteroaryl substituent, aralkyl substituent, or heteroarylalkyl substituent, Cl, Br, or CN. Preferably at least one of substituents $R^{1a}$ and $R^{2a}$ and at least one of substituents $R^{3a}$ and $R^{4a}$ is hydrogen; particularly preferably, three of substituents $R^{1a}$ to $R^{4a}$ are hydrogen. In addition, one of substituents $R^{3a}$ and $R^{4a}$ is preferably an aryl substituent or heteroaryl substituent, particularly preferably an aryl substituent.

The alkyl substituent, or the alkyl portion of these substituents, preferably comprises a linear chain of 1 to 20 carbon atoms. It may be substituted with one or more substituents, e.g. one, two, or three, selected from linear alkyl chains having up to 10 carbon atoms, Cl, Br, or CN, but is preferably unsubstituted.

The aryl substituent, or the aryl portion of the aralkyl substituent, is preferably phenyl or naphthyl, in particular phenyl. The heteroaryl substituent, or the heteroaryl portion of the heteroaralkyl substituent, is preferably pyridine or thiophene.

$R^{5a}$ is preferably selected from hydrogen, an alkyl substituent, an alkoxy substituent, an aryl substituent, heteroaryl substituent, aralkyl substituent, or heteroaralkyl substituent. Particularly preferably, $R^{5a}$ is an aryl substituent or heteroaryl substituent, in particular an aryl substituent.

The alkyl substituent, or the alkyl portion of these substituents, preferably comprises a linear chain of 1 to 20 carbon atoms. It may be substituted with one or more substituents, e.g. one, two, or three, selected from linear alkyl chains having up to 10 carbon atoms, Cl, Br, or CN, but is preferably unsubstituted.

The aryl substituent, or the aryl portion of the aralkyl substituent, is preferably phenyl or naphthyl. The heteroaryl substituent, or the heteroaryl portion of the heteroaralkyl substituent, is preferably pyridine or thiophene.

$R^{6a}$ and $R^{7a}$ are preferably selected, each independently, from hydrogen, an alkyl substituent, an alkyl substituent in which one or more $CH_2$ groups are replaced by a group selected independently from O, S, and phenylene, an alkoxy substituent, an aryl substituent, heteroaryl substituent, aralkyl substituent, or heteroarylalkyl substituent, Cl, Br, or CN.

The alkyl substituent, or the alkyl portion of these substituents, preferably comprises a linear chain of 1 to 12 carbon atoms, such that the carbon atoms may be replaced as described above. It may be substituted with one or more substituents, e.g. one, two, or three, selected from linear alkyl chains having up to 10 carbon atoms, Cl, Br, or CN, but is preferably unsubstituted.

The aryl substituent, or the aryl portion of the aralkyl substituent, is preferably phenyl or naphthyl, in particular phenyl. The heteroaryl substituent, or the heteroaryl portion of the heteroaralkyl substituent, is preferably pyridine or thiophene.

$R^{6a}$ is particularly preferably selected from an alkyl substituent, an alkyl substituent in which one or more $CH_2$ groups are replaced by phenylene or bisphenylene, an aryl substituent, heteroaryl substituent, aralkyl substituent, or heteroaralkyl substituent, and $R^{7a}$ is preferably hydrogen.

As explained above, $R^{6a}$ is particularly suitable as a linker group with which the compound of formula (IV) may be linked to a chromophore. In this case substituent $R^{6a}$ is a divalent substituent that is obtained formally by abstraction of a hydrogen atom from the aforementioned substituents.

In order to prepare a perylene bisimide dyad of formula (I), an olefin may be synthesized in a 1,3-dipolar cycloaddition from a nitrone of formula (II) and an olefin. Nitrones of formula (II) may be synthesized starting from a perylene-3, 4:9,10-tetracarboxylic acid bisimide which carries an aldehyde function that is coupled via the -X- group to an imide nitrogen atom (H. Langhals et al., Eur. J. Org. Chem., 2007, 4328-4336). The aldehyde is reacted with a hydroxylamine derivative, e.g. N-methylhydroxylamine and N-phenylhydroxylamine, with the result that the nitrone of formula (III) is obtained.

The synthesis of compounds of formulas (I) and (II) is shown by way of example in FIGS. 1 and 2. The starting material used in FIG. 1 is the aldehyde 2 (H. Langhals et al., Eur. J. Org. Chem. 2007, 4328-4336), and it is reacted with N-methylhydroxylamine to yield the methyl nitrone 3. Fluorescence is quenched in 3, so that the compound already formally meets the criteria for light-driven charge separation, but stability is lower than that of compounds of formula (I). A reaction with styrene was not possible with the 1,3- dipole 3. It is possible, however, by reacting 2 with phenylhydroxylamine, to synthesize the more reactive N-phenyl derivative 4, which reacts readily with an excess of styrene to produce 5, which is obtained as a diastereomer pair 5a and 5b. As further examples, the olefins methyl methacrylate and crotonic acid methyl ester were reacted to yield the isoxazolidines 6 and 7, for each of which a diastereomer was obtained (see FIG. 2). Acrylonitrile also reacts readily with 4 and forms the regioisomer pair 8 and 9.

FIG. 3 shows, by way of example, the synthesis of a compound of formula (I) and of formula (II) in which the phenyl spacer is replaced by a biphenyl spacer. A reaction, analogous to 3, of 10 with N-methylhydroxylamine to the nitrone 11 was possible without difficulty. The reactivity of the nitrone is so low, however, that when reacted with styrene its decomposition reactions are predominant. The aldehyde 10 was therefore reacted in the presence of styrene with N-phenylhydroxylamine, so that the resulting nitrone was captured directly. With this approach the isoxazolidine 12 may be obtained as a diastereomer pair 12a and 12b. The two diastereomers may be expected to have extraordinarily similar properties, meaning that for the vast majority of applications a separation is not necessary.

The UV/Vis absorption spectra of the tested compounds of formula (I) and (II) are identical in the visible spectral region, and deviate only by half a nanometer from the spectrum of dye 1a that carries two sec alkyl groups on the nitrogen atoms. In the UV region the differences are somewhat more pronounced (see FIG. 5). For example, below 300 nm the biphenyl spacer makes a considerable contribution to the absorption. The differences in the spectra of the other derivatives are less pronounced even in this spectral region, so that the substances are interchangeable in terms of spectra. Because the spectra of the various derivatives are practically identical, an electronic decoupling of the chromophore and functional unit can be assumed, since otherwise a feedback effect would have to occur.

The fluorescence of the compounds of formula (I) is, surprisingly, quenched. Given the aforementioned strong fluorescence of the amine derivatives, the efficiency of this quenching is astonishing and noteworthy. As a possible explanation, the fluorescence quenching can be attributed to an electron transfer from the isoxazolidine unit, which is electron-rich because of the α-effect, to the optically excited perylene unit (see FIG. 4). The HOMO of the electronic ground state, which is only half filled as a result of the optical excitation, is once again completely filled by means of the electron transfer. A return of the excited electron into its original orbital, accompanied by light emission, is thus suppressed and the fluorescence is quenched. It is not only the fluorescence of the compounds having a single phenyl spacer between the chromophore and the isoxazolidine unit that is quenched, but also in the case of compounds in which longer spacer groups, such as a biphenyl spacer, are present. Here the spacing between the electron donor and electron acceptor is already substantially greater, and charge separation thus occurs over a considerable distance. Electron transfer thus occurs very efficiently.

Fluorescence quenching in the compounds of formula (I) by electron transfer can be unequivocally distinguished experimentally from predissociation processes as an alternative possibility. For example, if the isoxazolidine 5 (FIG. 1) is protonated with trifluoroacetic acid or complexed with boron trifluaride etherate, the α-effect interaction is abolished by blockage of the free electron pair on the nitrogen atom, and furthermore the location of the non-bonding orbitals of the oxygen atom linked thereto is also lowered; on the other hand, there is only an insignificant change in the strength of the N-O bond as a result of protonation. This protonation switches the fluorescence of the dye completely on, and this therefore unequivocally verifies an electron transfer promoted by the α-effect. The isoxazolidines, constituting bases having a $pK_a$ of 5 to 6 (H. Langhals, T. Becherer, J. Lindner, A. Obermeier, Eur. J. Org. Chem., 2007, 4328-4336) can accordingly in fact be used as fluorescent indicators.

The light-driven charge separation in the compounds according to the present invention is extremely interesting for technical uses, since charge separations play a central role not only in the photosynthesis reaction center but also in systems for photovoltaic energy conversion. The comparatively large spacing between the separated charges is favorable for further transport for utilization, since it makes recombination, which would convert the absorbed energy into heat, more difficult.

For technical utilization in photovoltaics, for example, compounds according to the present invention of formula (I) can be incorporated directly into layer systems. It is even more ingenious to fasten the charge-separating structure on a surface, for example by 1,3-dipolar cycloaddition. For example, in this instance a metal surface that readily gives up electrons, such as e.g. aluminum, magnesium, or calcium, may be coated with a styrene derivative that carries an anchor group such as, for example, a carboxylate group. If 1,3-dipolar cycloaddition is then carried out using a perylene nitrone of formula (II), for example 4, the isoxazolidine thereby formed is then located directly on the metal surface (K. Rueck-Braun, T. E. H. Freysoldt, F. Wierschem, *Chem.*

Soc. Revs. 2005, 34, 507-516). As an alternative, isoxazolidines of this kind having anchor groups may also be conventionally constructed, and then brought into contact with a metal surface so they are bound there. When the metal surface is brought into contact with a more lipophilic medium, an increased interaction with that medium can then be expected. Ideally, the chromophores bound via isoxazolidines then become upright and project into the medium. Optimum charge separation away from the metal surface is thus achieved, and an electrically conductive medium can then pick up the charge of the perylene chromophore. A photovoltaic system of this kind is of particular interest, for example, because in the light-absorbing region it is made up exclusively of hydrogen, carbon, oxygen, and nitrogen, and can therefore be disposed of without difficulty after use. The perylene dyes used as a light-absorbing structure are extraordinarily light-fast (they are among the most light-fast of all fluorescent dyes) so that a very long service life for the system can be achieved. Because the novel dye systems of formulas (I) and (II) involve soluble substances, they can be applied as a solution onto the surfaces. This can be done, for example, by casting, spin-coating, or even by inkjet printing. The latter method furthermore offers the possibility of patterning the surface coverage at micrometer dimensions. This can be advantageous, for example, when the photovoltaic current needs to be taken off from individual small regions constituting individual solar cells or groups of such solar cells. This can offer the advantage, for example, that individual cells of the group can be shut off, for example if they have become defective, without negatively affecting the others. Also particularly advantageous is the flexibility of the organic materials, with which the solar cell systems can be adapted to curved surfaces, for example conventional roof tiles; this is almost impossible with the extremely brittle inorganic materials that are predominantly used at present.

The light-driven charge separation resulting from the novel dyes of formulas (I) and (II) can also be used in known titanium dioxide cells, of which the Grätzel cell is the most prominent. This type of solar cell usually uses an electrolyte as a medium, for example conventional liquid electrolytes such as liquids containing mineral salts, organic liquid electrolytes such as various imidazolium salts, or even solid electrolytes. The problem with these cells is that titanium dioxide absorbs not in the visible region but in the UV region, so that only a low energy yield results from irradiation with sunlight. What is needed here are adjuvants that absorb in the longer-wave region and bring about charge separation therein. The novel compounds of formulas (I) and (II) are tailor-made for such applications.

Lastly, the novel compounds of formulas (I) and (II) may also be combined with conventional silicon solar cells and thereby generate multi-layer'solar cells using organic material. The organic material may be used for efficient light-driven charge carrier injection into the silicon. The high molar absorption coefficient that can be achieved, and the ease of adaptation to various spectral regions, is a particular advantage of a coating having organic material. It is particularly worth noting in this context that the organic materials present no problems in terms of manufacture, handling, and disposal. It can in fact be removed from the silicon surface for recycling, so that pure silicon can be recovered.

In addition to photovoltaics, the charge separation may also be used for chemical reactions. For example, chemical reductions may be achieved using the light-induced radical anions of the perylene bisimides of formula (I), for example by carrying off, via electrodes or other devices, the positive charge of the isoxazolidines that is formed in complementary fashion. The isoxazolidine structures of formula (I) may be used in the same manner as oxidizing agents. It is thereby possible, for example, to obtain chemical process energy from solar radiation.

The present invention therefore also encompasses the use of the substances described here, in particular compounds of formulas (I) and (II), for the conversion of solar energy, typically in photovoltaic cells, as well as a photovoltaic cell that contains one of the compounds described here. An example that can be recited is, in particular, a titanium dioxide cell such as the Grätzel cell.

It also encompasses the use of the substances described here, in particular compounds of formulas (I) and (II), as light-driven reducing agents or oxidizing agents for chemical reactions.

It also encompasses the use of the substances described here, in particular compounds of formulas (I) and (II), as fluorescent indicators, e.g. for protonic acids, preferably mineral acids such as sulfuric acid, hydrochloric acid, nitric acid, and phosphoric acid, or for Lewis acids such as zinc chloride, anhydrous iron(II) chloride, anhydrous iron(III) chloride, and anhydrous aluminum chloride.

The nitrones of formula (II) in particular may moreover also be used as an indicator for olefins, since they can react with them via a 1,3-dipolar cycloaddition. To that extent a method for the detection of olefins is also a subject of the invention, comprising bringing a sample that is to be checked for the presence of an olefin into contact with a nitrone of formula (II). Preferred olefins are unsaturated fatty acids such as oleic acid, linoleic acid, and linolenic acid, or also their trans isomers which are known as trans fatty acids. The method may also be used, for example to distinguish cis fatty acids from trans fatty acids.

Further fields of application for the compounds of formula (I) are in general in sectors in which perylene dyes are utilized. Use in data media, preferably in optical storage media, may be mentioned by way of example; examples are systems such as CD or DVD discs, use in organic light-emitting diodes (OLEDs), use as pigments for tempera paints and related colors such as watercolors and water-based inks and inks for inkjet printers, paper colors, printing inks, inks and India inks and other colors for painting and writing purposes, and in coating materials, as pigments for lacquers; preferred lacquers are synthetic resin lacquers such as acrylic or vinyl resins, polyester resins, novolacs, nitrocellulose lacquers (nitro paints), or also natural substances such, as cellulose lacquer, shellac, or qi lacquer (Japanese lacquer or Chinese lacquer or East Asian lacquer), for mass coloring of polymers, for coloring natural substances, as mordant dyes, e.g. for dyeing natural substances, as coloring agents, e.g. for coloring paints, lacquers, and other coating materials, paper dyes, printing inks, inks, and other colors for painting and writing purposes, as pigments in electrophotography, or use for safety marking purposes, preferably for checks, check cards, banknotes, coupons, documents, identify papers, and the like.

EXAMPLES

General. IR spectra: Perkin Eimer 1420 Ratio Recording Infrared Spectrometer, FT 1000; UV/Vis spectra: Varian Cary 5000 and Bruins Omega 20; fluorescence spectra: Perkin Elmer FS 3000 (total correction); NMR spectroscopy: Varian VNMRS 600 (600 MHz); mass spectrometry: Finnigan MAT 95.

N-(1-Hexylheptyl)-N'-(4-N'''-methylcarbaldimine-N''-oxidobenzyl)perylene-3,4:9,10-tetracarboxylic acid bisimide (3): N-(4-Formylbenzyl)-N'-(1-hexylheptyl)perylene-3, 4:9,10-bis(dicarboximide) (2, obtained according to H. Langhals, T. Becherer, J. Lindner, A. Obermeier, *Eur. J. Org. Chem.* 2007, 4328-4336, 1.10 g, 1.59 mmol), N-methylhydroxylamine hydrochloride (200 mg, 2.39 mmol), and NaHCO$_3$ (287 mg, 3.31 mmol) were dissolved in CH$_2$Cl$_2$ (50 mL), had MgSO$_4$ (400 mg) added to it, was heated for 5 h under reflux, stirred for 16 h at room temperature, filtered, evaporated, and purified by column chromatography (silica gel, dichloromethane/methanol 30:1). Yield: 830 mg (65%) red solid, m.p. >300° C. R$_f$ (silica gel, dichloromethane/methanol 25:1)=0.30. IR (ATR): $\tilde{v}$=2955.4 m, 2919.5 s, 2854.0 m, 1692.4 s, 1647.1 s, 1591.7 s, 1574.5 m, 1505.8 w, 1465.8 w, 1435.8 m, 1402.5 m, 1353.1 m, 1337.1 s, 1250.4 m, 1171.9 m, 1127.2 w, 1109.4 w, 1005.5 w, 982.7 w, 851.2 w, 809.2 s, 744.5 m, 645.2 w cm$^{-1}$. $^1$H-NMR (600 MHz, CDCl$_3$, 25° C.):δ=0.83 (t, 1 H, $^3$J =6.8 Hz), 1.24-1.40 (m, 16 H, CH$_2$), 1.88-1.93 (m, 2 H, β-CH$_2$), 2.24-2.30 (m, 2 H, (β-CH$_2$), 3.88 (s, 3 H, CH$_3$), 5.16-5.21 (m, 1 H, CH—N), 5.42 (s, 2 H, CH$_2$—N), 7.33 (s, 1 H, CH—N), 7.60 (d, 1 H, $^3$J=7.1 Hz), 8.17 (d, 1 H, $^3$J=7.1 Hz), 8.57-8.68 ppm (m, 8 H, H$_{pery}$). $^{13}$C—NMR (150 MHz, CDCl$_3$, 25° C.):δ=14.3, 22.8, 27.2, 29.4, 32.0, 32.6, 43.8, 55.1, 123.1, 123.4, 126.5, 126.6, 128.9, 129.2, 129.6, 129.7, 130.0, 130.2, 131.3, 131.8, 132.0, 134.4, 135.1, 139.6, 163.5 ppm. UV/Vis (CHCl$_3$):λ$_{max}$ (E$_{rel}$)=529 (1.0), 492 (0.60), 463 nm (0.21). MS (DEI$^+$/ 70 eV): m/z (%)=720 (7)[M$^+$] 719 (14), 704 (17), 703 (38), 702 (24), 538 (15), 537 (19), 523 (22), 522 (64), 521 (100), 520 (21), 509 (14), 508 (21), 374 (14), 373 (26), 346 (18), 260 (10), 148 (13). C$_{46}$H$_{45}$N$_3$O$_5$ (719.9): calc. C, 76.75; H, 6.30; N, 5.84; obs. C, 76.69; H, 6.24; N, 5.66.

N-(1-Hexylheptyl)-N'-(4-N"-phenylcarbaldimine-N"-oxidobenzyl)perylene-3,4:9,10-tetracarboxylic acid bisimide (4): Formylbenzyl)-N'-(1-hexylheptyl)perylene-3,4:9,10-bis(dicarboximide) (2, obtained according to H. Langhals, T. Becherer, J. Lindner, A. Obermeier, *Eur. J. Org. Chem.* 2007, 4328-4336, 1.10 g, 1.59 mmol), and N-phenylhydroxylamine (200 mg, 1.83 mmol) were dissolved in CH$_2$Cl$_2$ (50 mL), had MgSO$_4$ (400 mg) added to them, were heated for 5 h under reflux, stirred for 16 h at room temperature, filtered, evaporated, and purified by column chromatography (silica gel, dichloromethane/methanol 30:1). Yield: 1.15 g (93%) red solid, m.p. >300° C. R$_f$ (silica gel, dichloromethane/methanol=25:1)=0.36. IR (ATR): $\tilde{v}$=3066.9 w, 2952.0 m, 2923.4 s, 2854.1 m, 1691.8 s, 1646.1 s, 1592.0 s, 1575.4 m, 1504.9 w, 1483.0 w, 1457.9 w, 1435.6 w, 1402.6 m, 1334.8 s, 1249.0 m, 1170.8 m, 1125.9 w, 1108.1 w, 1069.6 w, 1022.9 w, 987.3 w, 892.3 w, 850.5 w, 832.3 w, 809.6 m, 763.0 w, 684.9 w, 660.6 w, 622.5 w cm$^{-1}$. $^1$H-NMR(600 MHz, CDCl$_3$, 25° C.): δ=0.83 (t, 1 H, $^3$J=6.8 Hz, 6 H), 1.24-1.40 (m, 16 H, CH$_2$), 1.88-1.93 (m, 2 H, β-CH$_2$), 2.24-2.30 (m, 2 H, β-CH$_2$), 5.16-5.21 (m, 1 H, CH—N), 5.37 (s, 2 H, CH$_2$—N), 7.43-7.46 (m, 3 H, H$_{aryl}$), 7.66 (d, 1 H, $^3$J=8.4 Hz, H$_{aryl}$), 7.74 (d, 1 H, $^3$J=6.7 Hz, H$_{aryl}$), 7.90 (s, 1 H, CH—N), 8.24-8.36 ppm (m, 8 H, H$_{pery}$). $^{13}$C—NMR (150 MHz, CDCl$_3$, 25° C.): δ=14.0, 27.0, 29.2, 31.8, 32.4, 43.5, 54.9, 121.7, 122.7, 122.9, 123.3, 124.1, 125.9, 126.0, 129.0, 129.1, 129.2, 129.3, 129.3, 129.9, 130.1, 130.8, 131.2, 131.6, 133.8, 134.0, 134.4, 139.8, 149.0, 163.0, 163.3 ppm. UV/Vis (CHCl$_3$): λ$_{max}$ (ε)=463 (19600), 492 (53400), 529 nm (84300). MS (El$^+$/ 70 eV): m/z (%)=782 (10)[M$^+$+H], 767 (15), 766 (33), 690 (26), 584 (56), 583 (87), 509 (50), 508 (90), 374 (14), 346 (21), 285 (23), 284 (100), 210 (20), 209 (25), 208 (24). C$_{40}$H$_{41}$N$_7$O$_4$ (683.8): calc. C, 70.26; H, 6.04; N, 14.34; obs. C, 69.96; H, 5.89; N, 14.15.

N-(1-Hexylheptyl)-N'-(4-N"-methylcarbaldimine-N"-oxidobiphenyl)perylene-3,4:9,10-tetracarboxylic acid bisimide(11): N-(4-Carboaldehydebiphenyl-4'-methyl)-N'-(1-hexylheptyl)perylene-3,4:9,10-tetracarboxylic acid bisimide (10, 100 mg, 0.130 mmol) was dissolved in styrene (5 mL), had N-methylhydroxylamine hydrochloride (109 mg, 1.30 mmol) and sodium hydrogencarbonate (109 mg, 1.30 mmol) added to it, and was heated to 85° C. (slight gas evolution). The red solid precipitated after 30 minutes was filtered off and purified by column chromatography (silica gel, dichloromethane/methanol 30:1). Two byproducts and the starting material were quickly eluted, and then the reaction product as a red band. This was evaporated, dissolved in a little dichloromethane, precipitated with methanol, filtered off, and dried at room temperature. Yield: 53 mg (51%) red solid, m.p.>300 ° C. R$_f$ (silica gel, dichloromethane/methanol 30:1)=0.14. IR (ATR): $\tilde{v}$=2953.0 m, 2924.3 m, 2855.7 m, 1691.8 s, 1651.9 s, 1592.9 s, 1576.8 m, 1507.4 w, 1495.9 w, 1456.9 w, 1435.7 m, 1403.5 m, 1379.0 w, 1333.6 s, 1248.8 m, 1218.2 w, 1195.3 w, 1169.2 m, 1126.5 m, 1106.7 m, 1003.1 w, 988.4 w, 943.0 w, 853.3 m, 808.0 s, 782.8 m, 748.1 s, 721.2 m, 667.0 w, 639.5 m, 615.4 m, 587.4 m cm$^{-1}$. $^1$H-NMR (600 MHz, CDCl$_3$, 25° C.): δ=0.82 (t, $^3$J$_{H,H}$=7.0 Hz, 6 H, CH$_3$), 1.22-1.36 (m, 16 H, CH$_2$), 1.85-1.91 (m, 2.H, β-CH$_2$), 2.22-2.29 (m, 2 H, β-CH$_2$), 3.89 (s, 3 H, CH$_3$), 5.16-5.21 (tt, $^3$J$_{H,H}$=5.9 Hz, $^3$J$_{H,H}$=9.3 Hz, 1 H, α-CH), 5.42 (s, 2 H, CH$_2$—N), 7.38 (s, 1 H, CH=N), 7.54-7.61 (m, 8 H, H$_{arom}$), 8.48-8.54 ppm (m, 8H, H$_{perylene}$). $^{13}$C—NMR (150 MHz, CDCl$_3$, 25° C.): δ=14.0, 22.6, 27.0, 29.2, 29.9, 31.8, 32.4, 43.4, 54.9, 122.9, 123.0, 123.1, 123.2, 127.0, 127.2, 127.5, 127.6, 128.9, 129.3, 129.5, 129.6, 129.7, 129.7, 130.2, 131.6, 131.6, 134.1, 134.8, 134.9, 135.0, 135.2, 136.7, 137.4, 139.0, 139.5, 163.3, 163.4 ppm. UV/Vis (CHCl$_3$): λ$_{max}$ (E$_{rel}$)=463 (0.22), 492 (0.61), 529 nm (1.0). HRMS (C$_{52}$H$_{49}$N$_3$O$_5$): calc. m/z: 795.369, obs. m/z: 795.371, Δ=2 mmu.

N-(1-Hexylheptyl)-N'-4-(5-methyloxycarbonyl-5-methyl-2-phenylisoxazolidin-3-yl)benzylperylene-3,4:9,10-tetracarboxylic acid bisimide(6): N-(1-Hexylheptyl)-N'-(4-N"-phenylcarbaldimine-N"-oxidobenzyl)perylene-3,4:9,10-tetracarboxylic acid bisimide (4, 110 mg, 141 μmol) was suspended in methyl methacrylate (20 mL), heated to 60° C. (complete dissolution after 3 h), allowed to cool, evaporated under vacuum, and purified chromatographically (silica gel, CH$_2$Cl$_2$/MeOH 50:1). Yield: 87 mg (70%), m.p.>300° C. R$_f$ (silica gel, CH$_2$Cl$_2$/MeOH 50:1)=0.80. IR (ATR): $\tilde{v}$=2921 m, 2852 m, 1737 w, 1693 s, 1654 s, 1593 s, 1577 m, 1507 w, 1486 w, 1434 w, 1403 m, 1377 w, 1332 s, 1300 w, 1248 w, 1201 w, 1170 w, 1125 w, 1101 w, 1021 w, 981 w, 853 w, 809 m, 743 w, 694 w cm$^{-1}$. $^1$H-NMR (600 MHz, CDCl$_3$, 25° C.): δ=0.82 (t, 3 H, $^3$J=7.0 Hz, CH$_3$), 1.19-1.38 (m, 16 H, CH$_2$), 1.61 (s, 3 H, CH$_3$), 1.85-1.91 (m, 2 H, β-CH$_2$), 2.22-2.29 (m, 2 H, β-CH$_2$), 2.27 (dd, 1 H, $^3$J=7.4 Hz, $^2$J=12.5 Hz), 3.31 (dd, 1 H, $^3$J=8.9 Hz, $^2$J=12.5 Hz), 3.55 (s, 3 H, OCH$_3$), 5.16-5.21 (m, 1 H, α-CH), 4.74 (dd, 1 H, $^3$J=7.4 Hz, $^3$J=8.9 Hz), 5.39 (s, 2 H, N—CH$_2$), 6.81-6.83 (m, 1 H, H$_{aryl}$), 6.89-6.90 (m, 2 H, H$_{aryl}$), 7.18-7.13 (m, 2 H, H$_{aryl}$), 7.57 (d, 2 H, $^3$J=8.4 Hz), 7.43 (d, 2H, $^3$J=8.4 Hz), 8.53 (d, 2 H, $^3$J=8.1 Hz, H$_{perylene}$), 8.56 (d, 2 H, $^3$J=8.1 Hz, H$_{perylene}$), 8.62-8.67 ppm (m, 4 H, H$_{perylene}$). $^{13}$C—NMR (150 MHz, CDCl$_3$, 25° C.): δ=14.0, 22.5, 26.9, 29.2, 29.7, 31.8, 32.4, 43.4, 43.4, 49.8, 52.3, 54.8, 69.4, 83.2, 114.5, 117.0, 121.4, 122.9, 123.2, 124.1, 126.3, 126.6, 128.4, 129.6, 131.0, 131.0, 131.6, 134.2, 134.9, 136.4, 140.8, 151.1, 163.4, 164.6, 173.4 ppm. UV/Vis (CHCl$_3$): λ$_{max}$ (ε)=459.1 (18600), 491.0 (51400), 527.4 nm (85800). MS (DEI$^+$/70 eV): m/z (%): 690 (33) [M$^+$], 508 (100) [M$^+$–C$_{13}$H$_{26}$], 374 (14), [M$^+$–C$_{21}$H$_{35}$O$_2$], 346 (19) [M –C$_{22}$H$_{34}$NO$_2$], 44 (15) [CH$_2$NO]. HRMS (C$_{56}$H$_{55}$N$_3$O$_7$): calc. m/z 690.309, obs. m/z 690.308, Δ=1 mmu. C$_{56}$H$_{55}$N$_3$O$_7$ (882.1): calc. C, 76.25; H, 6.09; N, 4.76; obs. C, 75.88; H, 6.38; N, 4.59.

N-(1-Hexylheptyl)-N'-4-(5-phenyl-2-phenylisoxazolidin-3-yl)benzylperylene-3,4:9,10-tetracarboxylic acid bisimide (5): N-(1-Hexylheptyl)-N'-(4-N''-phenylcarbaldimine-N''-oxidobenzyl)perylene-3,4:9,10-tetracarboxylic acid bisimide (4, 120 mg, 153 µmol) was dissolved in styrene (10 mL), heated to 85° C., cooled after 1 h, evaporated under vacuum, and chromatographed (silica gel, $CH_2Cl_2$/MeOH 20:1, mixture of two diastereomers, de=77%). Yield: 102 mg (75%), m.p.>300° C. $R_f$ (silica gel, $CH_2Cl_2$MeOH 20:1)=0.79. IR (ATR): $\tilde{v}$=3604.9 w, 3036.7 w, 2954.5 m, 2924.2 m, 2855.3 m, 1691.5 s, 1655.3 s, 1593.0 m, 1577.8 s, 1508.3 w, 1484.6 w, 1436.1 m, 1403.7 s, 1351.8 s, 1332.5 s, 1300.6 m, 1249.1 s, 1251.8 w, 1169.9 m, 1127.1 w, 1104.9 w, 1082.7 w, 1020.7 w, 983.9 w, 924.9 w, 854.54 w, 810.2 s, 796.1 w, 771.8 m, 748.3 s, 696.2 s cm$^{-1}$. Main diastereomer: $^1$H-NMR (600 MHz, $CDCl_3$, 25° C.): δ=0.82 (t, 3 H, $^3J$=7.0 Hz, $CH_3$), 1.19-1.38 (m, 16 H, $CH_2$), 1.85-1.91 (m, 2 H, β-$CH_2$), 2.22-2.29 (m, 2 H, β-$CH_2$), 2.43 (ddd, 1 H, $^3J$=7.9 Hz, $^3J$=10.3 Hz, $^2J$=12.2 Hz, $CH_2$), 3.14 (ddd, 1 H, $^3J$=5.7 Hz, $^3J$=7.9 Hz, $^2J$=12.2 Hz, $CH_2$), 4.88 (t, 1 H, $^3J$=7.9 Hz, CH), 5.14 (dd, 1 H, $^3J$=5.7 Hz, $^3J$=10.3 Hz, CH), 5.16-5.21 (m, 1 H, α-CH), 5.39 (d, 1 H, N—$CH_2$), 5.42 (d, 1 H, N—$CH_2$), 6.88-6.91 (m, 1 H, $H_{aryl}$), 7.01 (d, 2 H, $^3J$=1.0 Hz, $H_{aryl}$), 7.02 (d, 2 H, $^3J$=1.0 Hz, $H_{aryl}$), 7.21 (d, 2 H, $^3J$=7.4 Hz, $H_{aryl}$), 7.23 (d, 2 H, $^3J$=7.4 Hz, $H_{aryl}$), 7.28-7.30 (m, 1 H, $H_{aryl}$), 7.32-7.35 (m, 2 H, $H_{aryl}$), 7.39-7.41 (m, 2 H, $H_{aryl}$), 7.52 (d, 2 H, $^3J$=8.4 Hz, $H_{aryl}$), 7.61 (d, 2 H, $^3J$=8.4 Hz, $H_{aryl}$), 8.52-8.65 ppm (m, 8 H, $H_{perylene}$). Secondary diastereomer: $^1$H-NMR (600 MHz, $CDCl_3$, 25° C.): δ=0.82 (t, 3 H, $^3J$=7.0 Hz, $CH_3$), 1.19-1.38 (m, 16 H, $CH_2$), 1.85-1.91 (m, 2 H, β-$CH_2$), 2.22-2.29 (m, 2 H, β-$CH_2$), 2.61 (ddd, 1 H, $^3J$=4.5 Hz, $^3J$=6.5 Hz, $^2J$=12.0 Hz, $CH_2$), 2.74 (td, 1 H, $^3J$=9.1 Hz, $^2J$=12.0 Hz, $CH_2$), 4.66 (dd, 1 H, $^3J$=4.5 Hz, $^3$=9.1 Hz, CH), 5.16-5.21 (m, 1 H, α-CH), 5.31 (dd, 1 H, $^3J$=6.5 Hz, $^3J$=9.1 Hz, CH), 5.39 (d, 1 H, N—$CH_2$), 5.42 (d, 1 H, N—$CH_2$), 6.88-6.91 (m, 1 H, $H_{aryl}$), 6.96 (d, 2 H, $^3J$=1.0 Hz, $H_{aryl}$), 6.97 (d, 2 H, $^3J$=1.0 Hz, $H_{aryl}$), 7.15 (d, 2 H, $^3J$=7.4 Hz, $H_{aryl}$), 7.17 (d, 2 H, $^3J$=7.4 Hz, $H_{aryl}$), 7.28-7.30 (m, 1 H, $H_{aryl}$), 7.32-7.35 (m, 2 H, $H_{aryl}$), 7.39-7.41 (m, 2 H, $H_{aryl}$), 7.52 (d, 2 H, $^3J$=8.4 Hz, $H_{aryl}$), 7.61 (d, 2 H, $^3J$=8.4 Hz, $H_{aryl}$), 8.52-8.65 ppm (m, 8 H, $H_{perylene}$). $^{13}$C-NMR (150 MHz, $CDCl_3$, 25° C.): δ=14.0, 22.6, 26.9, 29.2, 31.8, 32.4, 43.4, 47.2, 48.8, 54.8, 69.4, 71.4, 80.5, 113.9, 115.8, 122.9, 123.2, 126.5, 126.8, 128.5, 128.9, 129.6, 129.7, 131.0, 131.8, 134.2, 134.8, 136.2, 137.7, 142.4, 152.5, 163.4 ppm. UV/Vis ($CHCl_3$): $\lambda_{max}$ (ε)=459(18800), 491 (52100), 527 nm (85700). HRMS ($C_{59}H_{56}N_3O_5$): calc. m/z: 886.426, obs. m/z: 886.430, Δ=4 mmu. $C_{59}H_{55}N_3O_5 \cdot H_2O$ (885.4): calc. C, 78.38; H, 6.35; N, 4.65; obs. C, 78.17; H, 6.70; N, 4.34.

N-(1-Hexylheptyl)-N'-4-(5-cyano-2-phenylisoxazolidin-3-yl)benzylperylene-3,4:9,10-tetracarboxylic acid bisimide (8) And N-(1-hexylheptyl)-N'-4-(4-cyano-2-phenylisoxazolidin-3-yl)benzylperylene-3,4:9,10-tetracarboxylic acid bisimide (9): N-(1-Hexylheptyl)-N'-(4-N''-phenylcarbaldimine-N''-oxidobenzyl)perylene-3,4:9,10-tetracarboxylic acid bisimide (4, 110 mg, .153 µmol) was suspended in acrylonitrile (50 mL), boiled for 1 h under reflux, cooled, evaporated under vacuum, and chromatographed (silica gel, $CH_2Cl_2$/MeOH 45:1, mixture of two diastereomers, de=52%). Yield: 94 mg (73%). m.p.>300° C. $R_f$ (silica gel, $CH_2Cl_2$/MeOH 20:1)=0.79. Main diastereomer: $^1$H-NMR (600 MHz, $CDCl_3$, 25° C.): δ=0.82 (t, 3 H, $^3J$=7.0 Hz, $CH_3$), 1.19-1.38 (m, 16 H, $CH_2$), 1.85-1.91 (m, 2 H, β-$CH_2$), 2.22-2.29 (m, 2 H, β-$CH_2$), 2.47 (ddd, 1 H, $^3J$=3.9 Hz, $^3J$=5.9 Hz, $^2J$=12.8 Hz, $CH_2$), 3.15 (ddd, 1 H, $^3J$=3.9 Hz, $^3J$=9.0 Hz, $^2J$=12.8 Hz, $CH_2$), 4.47 (dd, 1 H, $^3J$=5.9 Hz, $^3J$=9.0 Hz, CH), 4.95 (dd, 1 H, $^3J$=3.9 Hz, $^3J$=9.0 Hz, CH), 5.16-5.21 (m, 1 H, α-CH), 5.41 (s, 2 H, N—$CH_2$), 6.94-6.95 (m, 3 H, $H_{aryl}$), 7.18-7.24 (m, 2 H, $H_{aryl}$), 7.49 (d, 2 H, $^3J$=8.3 Hz, $H_{aryl}$), 7.61 (d, 2 H, $^3J$=8.3 Hz, $H_{aryl}$), 8.55-8.66 ppm (m, 8 H, $H_{perylene}$). Secondary diastereomer: $^1$H-NMR (600 MHz, $CDCl_3$, 25° C.): δ=0.82 (t, 3 H, $^3J$=7.0 Hz, $CH_3$), 1.19-1.38 (m, 16 H, $CH_2$), 1.85-1.91 (m, 2 H, β-$CH_2$), 2.22-2.29 (m, 2 H, β-$CH_2$), 2.77 (ddd, 1 H, $^3J$=6.1 Hz, $^3J$=7.6 Hz, $^2J$=12.5 Hz, $CH_2$), 2.98 (ddd, 1 H, $^3J$=5.2 Hz, $^3J$=7.6 Hz, $^2J$=12.5 Hz, $CH_2$), 4.87 (dd, 1 H, $^3J$=5.2 Hz, $^3J$=7.6 Hz, CH), 4.95-4.97 (m, 1 H, CH), 5.16-5.21 (m, 1 H, α-CH), 5.41 (s, 2 H, N—$CH_2$), 6.94-6.95 (m, 3 H, $H_{aryl}$), 7.18-7.24 (m, 2 H, $H_{aryl}$), 7.49 (d, 2 H, $^3J$=8.3 Hz, $H_{aryl}$), 7.61 (d, 2 H, $^3J$=8.3 Hz, $H_{aryl}$), 8.55-8.66 ppm (m, 8 H, $H_{perylene}$). $C_{54}H_{50}N_4O_5$ (834.4): calc. C, 77.67; H, 6.04; N, 6.71; obs. C, 77.30; H, 5.89; N, 6.31.

N-(1-Hexylheptyl)-N'-4-(4-methyloxycarbonyl-5-methyl-2-phenylisoxazolidin-3-yl)benzylperylene-3,4:9,10-tetracarboxylic acid bisimide (7): N-(1-Hexylheptyl)-N'-(4-N''-phenylcarbaldimin-N''-oxidobenzyl)perylene-3,4:9,10-tetracarboxylic acid bisimide (4, 120 mg, 0.15 mmol) was suspended in crotonic acid methyl ester (20 mL), heated for 6 h at 65° C. (reflux), evaporated under vacuum, chromatographed (silica gel, dichloromethane/methanol 50:1, nonfluorescing bands), dissolved in a little chloroform, and precipitated with methanol. Yield: 80 mg (62.6%), light red solid, m.p.>300° C. $R_f$ (silica gel, dichloromethane/methanol 30:1)=0.82. IR (ATR): $\tilde{v}$=2935.4 w, 2923.6 m, 2853.9 m, 1736.0 w, 1693.4 s, 1654 s, 1592.7 s, 1577.5 m, 1507.3 w, 1486.1 w, 1434.1 m, 1403.2 m, 1376.9 w, 1331.6 s, 1247.3 m, 1216.2 w, 1169.3 w, 1124.5 w, 1105.0 w, 1020.8 w, 987.5 w, 851.8 w, 808.8 m, 744.0 m, 694.4 w cm$^{-1}$. $^1$H-NMR (600 MHz, $CDCl_3$, 25° C.): δ=0.82 (t, $^3J(H,H)$=7.0 Hz, 6 H, 2×$CH_3$), 1.23-1.30 (m, 16 H, 8×$CH_2$), 1.46 (d, $^3J(H,H)$=5.9 Hz, 3 H, $CH_3$), 1.81-1.88 (m, 2 H, β-$CH_2$), 2.21-2.27 (m, 2 H, β-$CH_2$), 3.12 (dd, $^3J(H,H)$=7.1 Hz, $^3J(H,H)$=9.2 Hz, 1 H, CH), 4.38 (qd, $^3J(H,H)$=5.9 Hz, $^3J(H,H)$=9.2 Hz, 1 H, CH), 5.10 (d, $^3J(H,H)$=7.1 Hz, 1 H, CH), 5.15-5.22 (m, 1 H, α-$CH_2$), 7.19-7.22 (m, 5 H, $CH_{aromat}$), 7.53 (dd, $^3J(H,H)$=6.2 Hz, 4 H, $CH_{aromat}$), 8.63-8.73 ppm (m, 8 H, $CH_{perylene}$). $^{13}$C-NMR (151 MHz, $CDCl_3$, 25° C.): δ=14.3, 22.8, 27.1, 29.4, 29.9, 32.0, 32.6, 55.0, 122.4, 123.8, 126.7, 129.1, 129.8, 131.9, 135.2, 136.7, 163.7 ppm. UV/Vis ($CHCl_3$): $\lambda_{max}$ (ε)=459 (21500), 490 (52400), 527 nm (84700). HRMS ($C_{56}H_{56}N_3O_5$): calc. m/z: 882.408; obs. m/z: 882.409. Δ=1 mmu. $C_{56}H_{55}N_3O_5$ (882.1): calc. C, 76.25; H, 6.28; N, 4.76; obs. C, 75.84; H, 6.16; N, 4.58.

N-(1-Hexylheptyl)-N'-4-(5-phenyl-2-phenylisoxazolidin-3-yl)biphenylmethylperylene-3,4:9,10-tetracarboxylic acid bisimide (12): N-(1-Hexylheptyl)-N'-(4-N''-methylcarbaldimine-N''-oxidobiphenyl)perylene-3,4:9,10-tetracarboxylic acid bisimide (10, 100 mg, 0.130 mmol) was dissolved in 5 mL styrene and had N-phenylhydroxylamine (142 mg, 1.30 mmol) added to it, was stirred for 25 h at 85° C., stirred for 40 h at room temperature, evaporated under vacuum, dissolved in dichloromethane, applied onto a chromatography column, chromatographed (silica gel, dichloromethane/methanol 70:1, first non-fluorescing band), precipitated with methanol from a little dichloromethane, filtered off, and dried at 110° C. (two diastereomers, de=28%). Yield: 34 mg (27%) red solid, m.p.>300° C. $R_1$ (silica gel, chloroform/ethanol=60:1)=0.28. IR (ATR): $\tilde{v}$=3066.9 w, 2952.0 m, 2923.4 m, 2854.1 m, 1691.8 s, 1646.1 s, 1592.0 s, 1575.4 m, 1483.0 w, 1457.9 w, 1435.6 w, 1402.6 w, 1334.8 s, 1249.0 m, 1170.8 m, 1125.9 w, 1108.1 w, 1069.6 w, 1022.9 w, 987.3 w, 892.3 w, 850.5 w, 832.3 w, 809.6 m, 763.0 w, 684.9 w, 660.6 w, 622.5 w cm$^{-1}$. Main diastereomer: $^1$H-NMR (600 Hz, $CDCl_3$, 25° C.): δ=0.82 (t, $^3J_{H,H}$=7.0 Hz, 6 H, $CH_3$), 1.21-1.36 (m, 16 H, $CH_2$), 1.84-1.90 (m, 2 H, β-$CH_2$), 2.20-2.28 (m, 2 H, β-$CH_2$), 2.50 (ddd, $^3J_{H,H}$=7.7 Hz, $^3J_{H,H}$=10.2 Hz, $^2J_{H,H}$=12.2 Hz, 1 H, $CH_2$), 3.20 (ddd, $^3J_{H,H}$=5.8 Hz, $^3J_{H,H}$=8.0 Hz, $^2J_{H,H}$=12.2 Hz, 1 H, CH$_2$), 4.95 (dd, $^3J_{H,H}$=7.8 Hz, 1 H, CH), 5.16-5.21 (m, 2 H, α-CH, CH), 5.46 (s, 2 H, CH$_2$—N), 6.93-7.72 (m, 18 H, H$_{arom}$), 8.63-8.73 ppm (m, 8 H, H$_{perylene}$). Secondary diastereomer(36%): H-NMR (600 Hz, CDCl$_3$, 25° C.): δ=0.82 (t, $^3J_{H,H}$=7.0 Hz, 6 H, CH$_3$), 1.21-1.36 (m, 16, CH$_2$), 1.84-1.90 (m, 2, β-CH$_2$), 2.20-2.28 (m, 2, β-CH$_2$), 2.69 (ddd, $^3J_{H,H}$=4.6 Hz, $^3J_{H,H}$=6.6 Hz, $^2J_{H,H}$=12.0, 1 H, CH), 2.78-2.83 (m, 1 H, CH), 4.72 (dd, $^3J_{H,H}$=4.6 Hz, $^3J_{H,H}$=6.6 Hz, 1 H, CH), 5.16-5.21(m, 1 H, α-CH), 5.34-5.39 (m, 1 H, CH), 5.46 (s, 2 H, CH$_2$—N), 6.93-7.72 (m, 18 H, H$_{arom}$), 8.63-8.73 ppm (m, 8 H, H$_{perylene}$). $^{13}$C-NMR (150 MHz, CDCl$_3$, 25° C.): δ=14.0, 22.6, 26.9, 29.2, 29.7, 31.8, 32.4, 43.5, 48.7, 54.8, 71.5, 80.8, 114.0, 121.4, 123.0, 126.7, 126.9, 127.2, 127.5, 128.6, 129.0, 129.5, 131.8, 135.0, 136.1, 137.8, 139.9, 140.2, 142.0, 152.5, 163.5 ppm. UV/Vis (CHCl$_3$): λ$_{max}$ (E$_{rel}$)=459 (0.21), 490 (0.60), 527 nm (1.0). HRMS (C$_{65}$H$_{60}$N$_3$O$_5$): calc. m/z: 962.456; obs. m/z: 962.459, Δ=3 mmu.

4-(1,3-Dioxolan-2-yl)-4-methylbenzonitrile [ cf. W. Korytnyk, N. Angelino, C. Dave, L. Caballas, *J. Med. Chem.* 1978, 27, 507-513]: 4-Cyanoacetophenone (5.0 g, 34.4 mmol) was dissolved in toluene (50 mL), had ethylene glycol (3.4 g, 55.1 mmol) and BF$_3$ etherate (0.5 mL) added to it dropwise, was heated on a water separator for 12 h under reflux, allowed to cool to room temperature (yellow reaction solution), had a 5-percent sodium hydrogencarbonate solution (40 mL) added, was extracted with diethyl ether, washed with saturated sodium chloride solution (30 mL), dried over MgSO$_4$, filtered, evaporated under vacuum, and recrystallized from diethyl ether/n-pentane (1:1), Yield: 2.2 g (34%) colorless solid, m.p. 70° C. $^1$H-NMR (200 MHz, CDCl$_3$, 25° C.): δ=1.62 (s, 3 H, CH$_3$), 3.72-3.75 (m, 2 H, CH$_2$), 4.02-4.08 (m, 2 H, CH$_2$), 7.57-7.64 ppm (m, 4 H, H$_{aryl}$). HRMS (C$_{11}$H$_{12}$NO$_2$): calc. m/z: 190.086, obs. m/z: 190.087, Δ=1 mmu.

4-(1,3-Dioxolan-2-yl)-4-methylbenzylamine [ cf. W. Korytnyk, N. Angelino, C. Dave, L. Caballas, *J. Med. Chem.* 1978, 21 ,507-513]: 4-(1,3-Dioxolan-2-yl)-4-methylbenzonitrile (2.00 g, 10.6 mmol) in diethyl ether (10 mL) was carefully added dropwise over 15 minutes, under argon at 0° C., into a suspension of lithium aluminum hydride (800 mg, 21.1 mmol) in diethyl ether (20 mL), stirred for 2 h at 0° C., stirred for 16 h at room temperature, had aqueous NaOH solution (2 N, 20 mL) carefully added to it dropwise, was extracted with ether (3×50 mL), dried over MgSO$_4$, filtered, and evaporated under vacuum. Yield: 1.32 g (64%) colorless liquid, n$^{20}_D$=1.552. $^1$H-NMR (200 MHz, CDCl$_3$, 25° C.): δ=1.63 (s, 3 H, CH$_3$), 3.72-3.75 (m, 2 H, CH$_2$), 3.84 (s, 2 H, N—CH$_2$) 4.02-4.08 (m, 2 H, CH$_2$), 7.26 (d, 2 H, $^3$J=8.3 Hz, H$_{aryl}$) 7.43 ppm (d, 2 H, $^3$J=8.3 Hz, H$_{aryl}$). MS (DEI$^+$/70 eV): m/z (%): 193 (5) [M$^+$], 178 (100), 134 (39), 87 (20), 43 (11).

N-[4-(2-Methyl[1,3]dioxolan-2-yl)benzyl]-N'-(1-hexylheptyl)perylene-3,4:9,10-tetracarboxylic acid bisimide: N-1-Hexylheptylperylene-1,3:9,10-tetracarboxylic acid-3,4-anhydride-9,10-carboxylic acid imide (270 mg, 0.47 mmol) was prepared in imidazole (5 g), heated to 140° C., had 4-(1,3-dioxolan-2-yl)-4-methylbenzylamine (110 mg, 0.56 mmol) added to it, was stirred for 3 h at 140° C., while still warm had a few milliliters of ethanol and 2 N hydrochloric acid (50 mL) added, was filtered off once completely cooled, washed with aqueous 2 N HCl, dried for 16 h in a drying cabinet at 110° C., dissolved in a little chloroform, and chromatographed (silica gel CHCl$_3$/EtOH 30:1). Yield: 246 mg (70%) red solid, m.p.>300° C. R$_f$ (silica gel, chloroform/ethanol 30:1)=0.17. IR (ATR): ṽ=2955.0 m, 2923.9 m, 2856.0 m, 1693.1 m, 1648.4 s, 1592.9 m, 1576.5 m, 1507.5 w, 1482.9 w, 1456.8 w, 1435.9 m, 1420.5 w, 1403.7 w, 1378.5 w, 1339.3 m, 1284.2 m, 1249.1 m, 1173.2 m, 1135.5 w, 1127.9 w, 1111.1 w, 1091.7 w, 1038.2 m, 1020.2 w, 983.8 w, 948.3 w, 862.4 w, 808.9 m, 781.1 w, 744.4 m, 725.4 w cm$^{-1}$. $^1$H-NMR (600 MHz, CDCl$_3$, 25° C.): δ=8.43-8.57 (m, 8 H, H$_{pery}$), 7.54 (d, 1 H, $^3$J=8.5 Hz), 7.44 (d, 1 H, $^3$J=8.5 Hz), 5.37 (s, 2 H, CH$_2$—N), 5.16-5.21 (m, 1 H, CH—N), 3.72-3.76 (m, 2 H, CH$_2$), 3.98-4.00 (m, 2 H, CH$_2$), 2.23-2.29 (m, 2 H, β-CH$_2$), 1.86-1.92 (m, 2 H, β-CH$_2$), 1.21-1.38 (m, 16 H, CH$_2$), 0.82 ppm (t, 1 H, $^3$J=7.0 Hz). $^{13}$C-NMR (150 MHz, CDCl$_3$, 25° C.): δ=163.2, 142.7, 136.6, 134.7, 131.7, 131.6, 129.4, 129.3, 129.1, 129.0, 128.6, 125.5, 123.1, 22.9, 122.9, 108.7, 64.4, 54.8, 43.4, 32.4, 31.8, 29.2, 27.6, 27.0, 22.6, 14.0 ppm. UV/Vis (CHCl$_3$): λ$_{max}$ (ε)=463 (81220), 492 (50320), 529 nm (18510). Fluorescence (CHCl$_3$): λ$_{max}$ (l$_{rel}$)=539 (1.00), 582 nm (0.40). Fluorescence quantum yield (CHCl$_3$, λ$_{exc}$=491 nm, E$_{491\ nm}$=0.0347 cm$^{-1}$, reference: 1a where φ=1.00): 1.00. MS (DEI$^+$/70 eV): m/z (%)=749 (21) [M$^+$+H], 748 [M$^+$] (38), 735 (13), 734 (47), 733 (100), 569 (12), 568 (18), 567 (21), 554 (11), 553 (34), 552 (41), 551 (43), 549 (13), 548 (31), 373 (11), 276 (12), 275 (30). C$_{48}$H$_{48}$N$_2$O$_6$ (748.9): calc. C, 76.98; H, 6.46; N, 3.74; obs. C, 77.05; H, 6.41; N, 3.58.

N-(4-Acetylbenzyl)-N'-(1-hexylheptyl)perylene-3,4:9,10-tetracarboxylic acid bisimide: For acetal cleavage, N-[4-(2-methyl[1,3]dioxolan-2-yl)benzyl]-N'-(1-hexylheptyl)perylene-3,4:9,10-tetracarboxylic acid bisimide (1.72 g, 2.30 mmol) was dissolved in tetrahydofuran (220 mL) at 70° C., had 2 N hydrochloric acid (50 mL) added to it, was heated for 5 h at 70° C., precipitated by adding 2 N hydrochloric acid, filtered off, rewashed, and dried at 110° C. Yield: 1.60 g (98%) red solid, m.p.>300° C. R$_f$ (silica gel, chloroform/ethanol 30:1)=0.83. IR (ATR): ṽ=2957.0 m, 2922.1 m, 2855.1 m, 1696.8 m, 1674.8 m, 1647.9 s, 1608.3 w, 1592.9 m, 1576.1 m, 1507.7 w, 1482.9 w, 1466.3 w, 1436.6 nn, 1403.7 m, 1379.4 w, 1336.4 s, 1310.1 m, 1251.0 m, 1192.4 w, 1171.6 m, 1124.9 w, 1114.6 w, 1076.7 w, 1019.5 w, 988.5 m, 956.4 w, 852.2 w, 839.8 m, 808.9 s; 796.4 w, 783.5 m, 745.6 s, 727.9 w, 683.9 w cm$^{-1}$. $^1$H-NMR (600 Hz, CDCl$_3$, 25° C.): δ=0.82 (t, 6 H, $^3J_{H,H}$=7.1 Hz, CH$_3$), 1.19-1.39 (m, 16 H, CH$_2$), 1.85-1.91 (m, 2 H, β-CH$_2$), 2.22-2.28 (m, 2 H, β-CH$_2$), 5.18 (tt, $^3J_{H,H}$=5.8 Hz, $^3J_{H,H}$=9.3 Hz, 1 H, α-CH), 5.44 (s, 2 H, CH$_2$—N), 7.77 (d, $^3J_{H,H}$=8.5 Hz, $^4J_{H,H}$=173.9 Hz, 4 H, H$_{arom}$), 8.55-8.65 ppm (m, 8 H, H$_{perylene}$). $^{13}$C-NMR (150 MHz, CDCl$_3$, 25° C.): δ=14.0, 22.6, 26.6, 27.0, 29.2, 29.7, 31.8, 32.4, 43.5, 54.9, 122.8, 123.0, 123.3, 126.3, 126.5, 128.6, 129.0, 129.5, 131.7, 134.1, 135.0, 136.4, 142.7, 163.3 ppm. UV/Vis (CHCl$_3$): λ$_{max}$ (ε)=462 (20570), 491 (51780), 527 nm (84530). Fluorescence (CHCl$_3$): λ$_{max}$ (ε)=539 (1.00), 582 nm (0.40). Fluorescence quantum yield (CHCl$_3$, λ$_{exc}$=491 nm, E$_{491\ nm}$=0.0294 cm$^{-1}$, reference: 1a with φ=1.00): 1.00. MS (DEI$^+$/70 eV): m/z (%)=705 [M$^+$+H] (24), 704 [M$^+$] (37), 524 (24), 523 (76), 522 (100), 508 (11), 507 (24), 390[M$^+$–C$_{13}$H$_{27}$–C$_9$H$_9$O] (7), 374 (15), 373 (9), 346 (12), 254 (11), 55 (8). HRMS (C$_{46}$H$_{44}$N$_2$O$_5$): calc. m/z: 704.327, obs. m/z: 704.330, Δ=3 mmu. C$_{46}$H$_{44}$N$_2$O$_5$ (704.3): calc. C, 78.38; H, 6.29; N, 3.97; obs. C, 77.96; H, 6.21; N, 3.91.

What is claimed is:
1. Perylene bisimide dyads of the general formula (I),

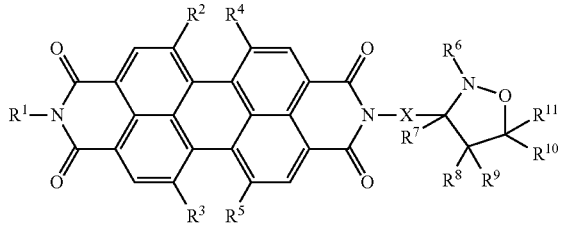

wherein
substituents $R^1$ to $R^{11}$ are identical or different and denote, each independently, hydrogen or a linear alkyl substituent having at least one and at most 37 carbon atoms;
wherein in the alkyl substituent, one to 10 $CH_2$ units may be replaced, each independently, by a carbonyl group, an oxygen atom, sulfur atom, selenium atom, tellurium atom, a cis or trans CH=CH group in which one CH unit may also be replaced by a nitrogen atom, an acetylenic C≡C group, a divalent phenyl substituent, divalent pyridine substituent, divalent thiophene substituent, divalent naphthalene substituent in which one or two CH groups may be replaced by nitrogen atoms, and a divalent anthracene substituent in which one or two CH groups may be replaced by nitrogen atoms;
wherein up to 12 individual hydrogen atoms of the $CH_2$ groups may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent, a divalent pyridine substituent, a divalent thiophene substituent, a divalent naphthalene substituent in which one or two CH groups may be replaced by nitrogen atoms, and a divalent anthracene substituent in which one or two CH groups may be replaced by nitrogen atoms;
wherein up to 12 individual hydrogen atoms of the $CH_2$ groups in an alkyl substituent may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent, a divalent pyridine substituent, a divalent thiophene substituent, a divalent naphthalene substituent in which one or two CH groups may be replaced by nitrogen atoms, and a divalent anthracene substituent in which one or two CH groups may be replaced by nitrogen atoms;
wherein $CH_2$ groups on which a hydrogen atom is replaced as described above may also be linked to one another to form a ring;
wherein substituents $R^1$ to $R^5$ and $R^7$ to $R^{11}$ may moreover represent, each independently, the halogen atoms F, Cl, Br or I, or CN;
X in formula (I) signifies one to 12 $CH_2$ units in which, each independently, one or more may be replaced respectively by a carbonyl group, an oxygen atom, sulfur atom, selenium atom, tellurium atom, a cis or trans CH=CH group in which one CH unit may also be replaced by a nitrogen atom, an acetylenic C≡C group, a divalent phenyl substituent, a divalent pyridine substituent, a divalent thiophene substituent, a divalent naphthalene substituent in which one or two CH groups may be replaced by nitrogen atoms, and a divalent anthracene substituent in which one or two CH groups may be replaced by nitrogen atoms;
wherein up to 12 individual hydrogen atoms of the $CH_2$ groups' may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent, divalent pyridine substituent, divalent thiophene substituent, divalent naphthalene substituent in which one or two CH groups may be replaced by nitrogen atoms, and a divalent anthracene substituent in which one or two CH groups may be replaced by nitrogen atoms;
wherein up to 12 individual hydrogen atoms of the $CH_2$ groups of the alkyl substituents may be replaced, in each case each independently even on identical carbon atoms, by the halogens fluorine, chlorine, bromine, or iodine, a cyano group, or a linear alkyl chain having up to 18 carbon atoms in which one to six $CH_2$ units may be replaced, each independently, by a carbonyl group, an oxygen atom, sulfur atom, selenium atom, tellurium atom, a cis or trans CH=CH group in which one CH unit may be replaced by a nitrogen atom, an acetylenic C≡C group, a divalent phenyl substituent, divalent pyridine substituent, divalent thiophene substituent, divalent naphthalene substituent in which one or two CH groups may be replaced by nitrogen atoms, and a divalent anthracene substituent in which one or two CH groups may be replaced by nitrogen atoms; and
wherein $CH_2$ groups on which a hydrogen atom is replaced as described above may also be linked to one another to form a ring.

2. The compound according to claim 1, wherein substituents $R^1$ to $R^5$ are selected from hydrogen and a hydrocarbon substituent.

3. The compound according to claim 1, wherein $R^6$ is selected from an aryl substituent or heteroaryl substituent.

4. The compound according to claim 1, wherein X is a group that is constituted from one or two phenylene groups or one bisphenylene group in combination with one to four methylene units.

5. A method for manufacturing a perylene bisimide dyad, wherein an olefin is reacted by 1,3-dipolar cycloaddition with a nitrone, wherein the perylene bisimide is a perylene bisimide of formula (I) according to claim 1 and the nitrone is a nitrone of formula (II),

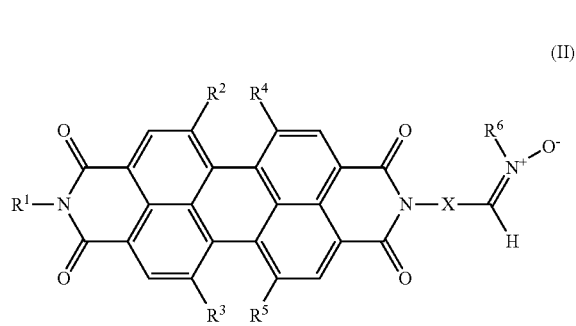

(II)

wherein $R^1$ to $R^6$ and X have the same meaning as in formula (I).

6. A photovoltaic cell comprising a compound according to claim 1.

7. The photovoltaic cell according to claim 6, wherein the photovoltaic cell is a titanium oxide cell.

8. A method for converting solar energy into electrical energy comprising using a system for light-driven charge separation comprising a compound according to claim 1 in the presence of solar energy.

9. A method for carrying out a chemical reaction comprising using a compound according to claim 1 as a light-driven reducing or oxidizing agent in a chemical reaction in the presence of light.

10. A method for detecting protonic acids and Lewis acids comprising using a compound according to claim 1 as a fluorescent indicator.

* * * * *